US012662574B2

(12) United States Patent
Dong et al.

(10) Patent No.: US 12,662,574 B2
(45) Date of Patent: Jun. 23, 2026

(54) MONOMERS FOR NON-ISOCYANATE POLYURETHANES

(71) Applicant: Alliance for Energy Innovation, LLC, Golden, CO (US)

(72) Inventors: Tao Dong, Lakewood, CO (US); Cheng Zhang, Golden, CO (US)

(73) Assignee: Alliance for Energy Innovation, LLC, Golden, CO (US)

( * ) Notice: Subject to any disclaimer, the term of this patent is extended or adjusted under 35 U.S.C. 154(b) by 678 days.

(21) Appl. No.: 18/190,850

(22) Filed: Mar. 27, 2023

(65) Prior Publication Data

US 2023/0303771 A1 Sep. 28, 2023

Related U.S. Application Data

(60) Provisional application No. 63/323,950, filed on Mar. 25, 2022.

(51) Int. Cl.

| | |
|---|---|
| ***C08G 71/04*** | (2006.01) |
| ***C07D 317/38*** | (2006.01) |
| ***C07D 407/14*** | (2006.01) |
| ***C08G 64/02*** | (2006.01) |

(52) U.S. Cl.

CPC ........... *C08G 71/04* (2013.01); *C07D 317/38* (2013.01); *C07D 407/14* (2013.01); *C08G 64/0208* (2013.01)

(58) Field of Classification Search

None

See application file for complete search history.

(56) References Cited

FOREIGN PATENT DOCUMENTS

WO WO-2022128822 A1 * 6/2022 ............. C08G 71/04

OTHER PUBLICATIONS

Aduba, Jr. et al., "Electrospinning of Plant Oil-Based, Non-Isocyanate Polyurethanes for Biomedical Applications", Journal of Applied Polymer Science, 2018, vol. 135, No. 29, pp. 1-11.

Bähr et al., "Linseed and Soybean Oil-Based Polyurethanes Prepared via the Non-Isocyanate Route andCatalytic Carbon Dioxide Conversion", Green Chemistry, 2012, vol. 14, No. 2, 483-489.

Beniah et al., "Novel thermoplastic polyhydroxyurethane elastomers as effective damping materials over broad temperature ranges", European Polymer Journal, 2016, vol. 84, pp. 770-783.

(Continued)

*Primary Examiner* — Eli D. Strah

(74) *Attorney, Agent, or Firm* — Michael A. McIntyre

(57) ABSTRACT

The present disclosure relates to a composition that includes a structure as defined by

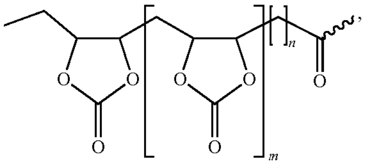

where 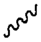 includes a covalent bond, n is between 0 and 20, inclusively, and m is between 0 and 20, inclusively.

9 Claims, 13 Drawing Sheets

(56) References Cited

OTHER PUBLICATIONS

Beniah et al., "Combined Effects of Carbonate and Soft-Segment Molecular Structures on the Nanophase Separation and Properties of Segmented Polyhydroxyurethane", Macromolecules, 2017, vol. 50, No. 8, pp. 3193-3203.
Beniah et al., "Functionalization of hydroxyl groups in segmented polyhydroxyurethane eliminates nanophase separation", Journal of Polymer Science Part A: Polymer Chemistry, 2017, vol. 55, pp. 3347-3351.
Beniah et al., Non-Isocyanate Polyurethane Thermoplastic Elastomer: Amide-Based Chain Extender Yields Enhanced Nanophase Separation and Properties in Polyhydroxyurethane. Macromolecules, 2017, vol. 50, pp. 4425-4434.
Błażek et al., "Diamine derivatives of dimerized fatty acids and bio-based polyether polyolas sustainable platforms for the synthesis of non-isocyanate polyurethanes", Polymer, 2020, vol. 205, No. 122768, pp. 1-14.
Cakić et al., "Crystallization and thermal properties in waterborne polyurethane elastomers: Influence of mixed soft segment block", Materials Chemistry and Physics, 2014, vol. 144, pp. 31-40.
Desroches et al., "Synthesis of Bio-Based Building Blocks fromVegetable Oils: A Platform Chemicals Approach", Lipid Technology, 2014, vol. 26, No. 2, pp. 35-38.
Dong et al., "Assessment of Plant and Microalgal Oil-Derived Nonisocyanate Polyurethane Products for Potential Commercialization", ACS Sustainable Chemistry & Engineering, 2021, vol. 9, No. 38, pp. 12858-12869.
Engels et al., "Polyurethanes: versatile materials and sustainable problem solvers for today's challenges", Angewandte Chemie International Edition, 2013, vol. 52, No. 36, pp. 9422-9441.
He et al., "Lipase-Catalyzed Synthesis, PropertiesCharacterization, and Application of Bio-Based Dimer Acid Cyclocarbonate", Polymers, 2018, vol. 10, No. 262, pp. 1-13.
Ghasemlou et al., "Bio-based routes to synthesize cyclic carbonates and polyamines precursors of non-isocyanate polyurethanes: A review", European Polymer Journal, Sep. 2019, vol. 118, pp. 668-684.
Jiang et al., "Phase Separation and Crystallization in High Hard Block Content Polyurethane Thin Films", Macromolecules, 2015, vol. 48, No. 15, pp. 5358-5366.
Korley et al., "Effect of the degree of soft and hard segment ordering on the morphology and mechanical behavior of semicrystalline segmented polyurethanes", Polymer, 2006, vol. 47, No. 9, pp. 3073-3082.
Leitsch et al., "Nonisocyanate Thermoplastic Polyhydroxyurethane Elastomers via Cyclic Carbonate Aminolysis: Critical Role of Hydroxyl Groups in Controlling Nanophase Separation", ACS Macro Letters, 2016, vol. 5, pp. 424-429.
Ling et al., "Synthesis and characterization of 1 K waterborne non-isocyanate polyurethane epoxy hybrid coating", Progress in Organic Coatings, Aug. 2022, vol. 169, pp. 1-9.
Maisonneuve et al., "Novel Green Fatty Acid-Based Bis-Cyclic Carbonates for the Synthesis of Isocyanate-Free Poly(Hydroxyurethane Amide)S", RSC Advances, 2014, vol. 4, No. 49, pp. 25795-25803.
Maisonneuve et al., "Isocyanate-Free Routes to Polyurethanes and Poly(hydroxy Urethane)s", Chemical Reviews, 2015, vol. 115, No. 22, pp. 12407-12439.
Matsukizono et al., "Synthesis and hydrolytic properties of water-soluble poly(carbonate-hydroxyurethane)s from trimethylolpropane", Polymer Chemistry, 2016, vol. 7, No. 4, pp. 958-969.
Matsukizono et al., "Synthesis of Bi- and Trifunctional Cyclic Carbonates Based on Trimethylolpropane and Their Application to Networked Polyhydroxyurethanes", Journal of Materials Science Research, 2016, vol. 5, No. 3, pp. 11-28.
Matsukizono et al., "Reworkable Polyhydroxyurethane Films with Reversible Acetal Networks Obtained from Multifunctional Six-Membered Cyclic Carbonates", Journal of the American Chemical Society, 2018, vol. 140, No. 3, pp. 884-887.
Miloslavskiy et al., "Cyclic Carbonates Based on Vegetable Oils", International Letters of Chemistry, Physics and Astronomy, 2014, vol. 8, No. 27, pp. 20-29.
Ochiai et al., "Nucleophilic polyaddition in water based on chemo-selective reaction of cyclic carbonate with amine", Green Chemistry, 2005, vol. 7, No. 11, pp. 765-767.
Ochiai et al., "Salt effect on polyaddition of bifunctional cyclic carbonate and diamine", Journal of Polymer Science Part A: Polymer Chemistry, 2005, vol. 43, No. 24, pp. 6282-6286.
Rix et al., "Synthesis of fatty acid-based non-isocyanate polyurethanes, NIPUs, in bulk and mini-emulsion", European Polymer Journal, 2016, vol. 84, pp. 863-872.
Rokicki et al., "Non-isocyanate polyurethanes: synthesis, properties, and applications", Polymers for Advanced Technologies, May 2015, vol. 26, No. 7, pp. 707-761.
Stachak et al., "Recent Advances in Fabrication of Non-Isocyanate Polyurethane-Based Composite Materials. Materials (Basel)", Materials, 2021, vol. 14, No. 13, pp. 1-27.
Sonnenschein et al., "Enhancing polyurethane properties via soft segment crystallization", Polymer, 2005, vol. 46, No. 23, pp. 10158-10166.
Tomita et al., "Model Reaction for the Synthesis of Polyhydroxyurethanes from Cyclic Carbonates with Amines: Substituent Effect on the Reactivity and Selectivity of Ring-Opening Direction in the Reaction of Five-Membered Cyclic Carbonates with Amine", Journal of Polymer Science: Part A: Polymer Chemistry, Nov. 2001, vol. 39, No. 21, pp. 3678-3685.
Yu et al., "Catalyzed Non-Isocyanate Polyurethane (NIPU) Coatings from Bio-Based Poly(Cyclic Carbonates)", Journal of Coatings Technology and Research, 2019, vol. 16, No. 1, pp. 41-57.
Zhang et al., "Non-IsocyanatePoly(Amide-Hydroxyurethane)s from Sustainable Resources", Green Chemistry, 2016, vol. 18, No. 17, pp. 4667-4681.
Zhang et al., "High Biobased Carbon Content Polyurethane Dispersions Synthesized from Fatty Acid-Based Isocyanate", Industrial & Engineering Chemistry Research, 2019, vol. 58, pp. 5195-5201.
Zhang et al., "Anti-corrosion non-isocyanate polyurethane polysiloxane organic/inorganic hybrid coatings", Progress in Organic Coatings, Nov. 2020, vol. 148, pp. 1-8.

* cited by examiner

MONOMERS FOR NON-ISOCYANATE POLYURETHANES

CROSS-REFERENCE TO RELATED APPLICATIONS

This application claims priority from U.S. Provisional Patent Application No. 63/323,950 on Mar. 25, 2022, the contents of which are incorporated herein by reference in their entirety.

CONTRACTUAL ORIGIN

This invention was made with government support under Contract No. DE-AC36-08GO28308 awarded by the Department of Energy. The government has certain rights in the invention.

BACKGROUND

Non-isocyanate polyurethanes (NIPUs) are a new generation of environmentally friendly polyurethane (PU) materials with many potential applications. To attain a carbon-neutral future, there is a growing interest in bio-based NIPUs to replace petroleum-based PU. Linseed oil provides an appealing low cost, bio-based, and eco-friendly platform for producing NIPUs. However, the high viscosity of cyclic carbonated linseed triglyceride (linseed TAG) restricts their use in industrial applications. Thus, there remains a need for alternative biobased raw materials for producing new NIPU compositions that are both reliable and economically viable at industrial scales.

SUMMARY

An aspect of the present disclosure is a composition that includes a structure as defined by

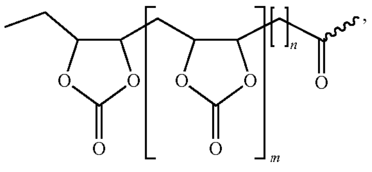

where  includes a covalent bond, n is between 0 and 20, inclusively, and m is between 0 and 20, inclusively. In some embodiments of the present disclosure, the structure may be

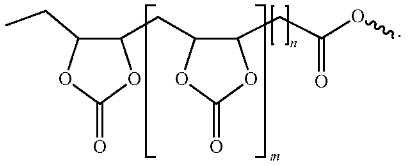

In some embodiments of the present disclosure, the structure may include at least one of

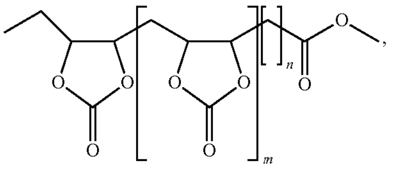

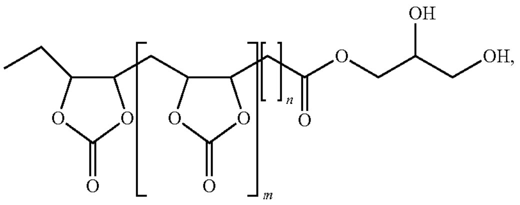

and/or

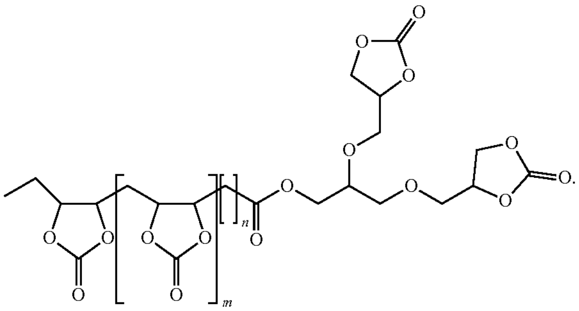

In some embodiments of the present disclosure, the structure may be

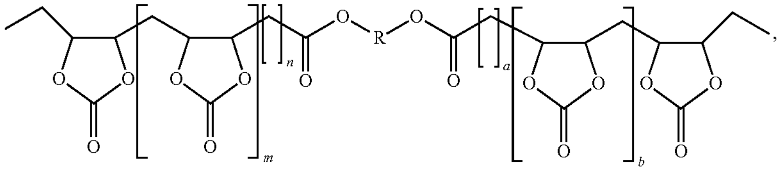

where R includes at least one of carbon, hydrogen, and/or oxygen, a may be between 0 and 30, inclusively, b may be between 0 and 20, inclusively, n may be between 0 and 30, inclusively, and m may be between 0 and 20, inclusively. In some embodiments of the present disclosure, the structure may be defined by

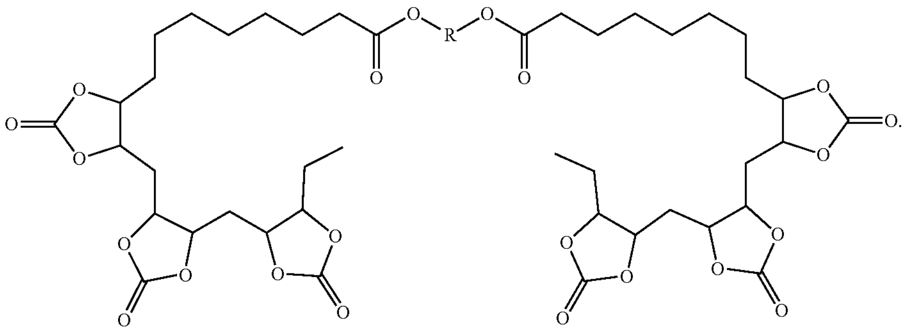

In some embodiments of the present disclosure, R may include

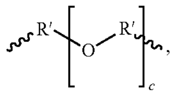

c may be between 0 and 500, inclusively, and R' may be a straight hydrocarbon chain having between 1 and 18 carbon atoms, inclusively. In some embodiments of the present disclosure, R may be defined by

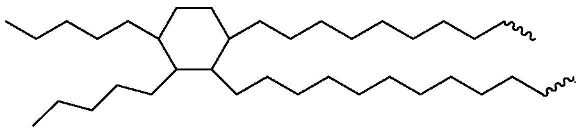

In some embodiments of the present disclosure, the structure may be defined by at least one of

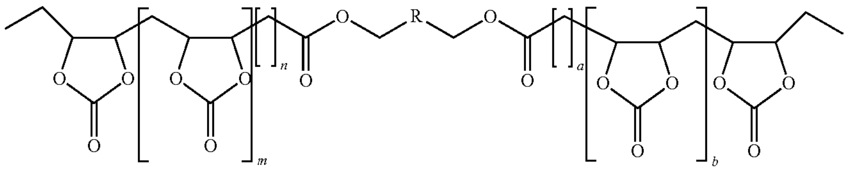

and/or

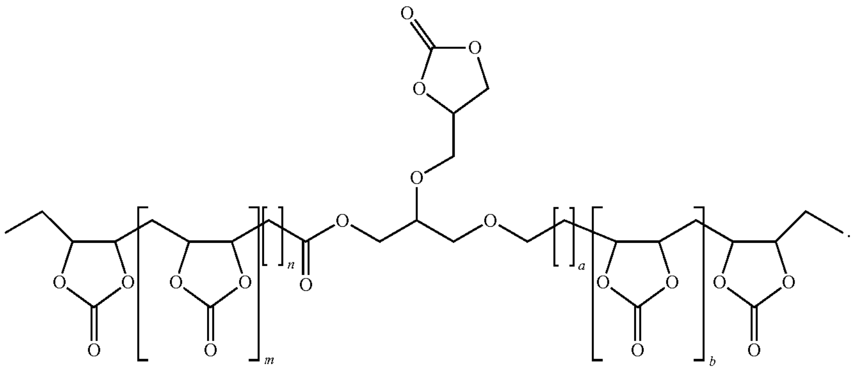

In some embodiments of the present disclosure, the structure may be defined by

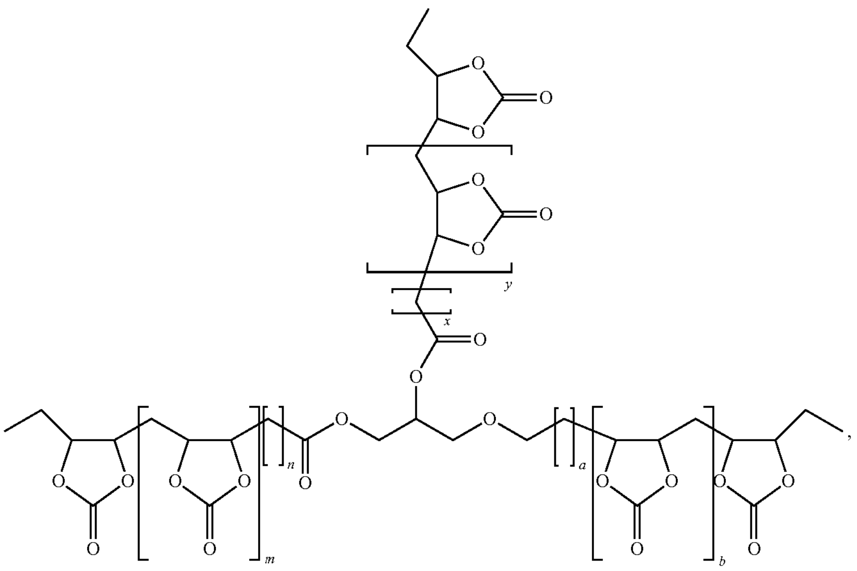

where x may be between 0 and 20, inclusively, and y may be between 0 and 20, inclusively.

In some embodiments of the present disclosure, the structure may be defined by

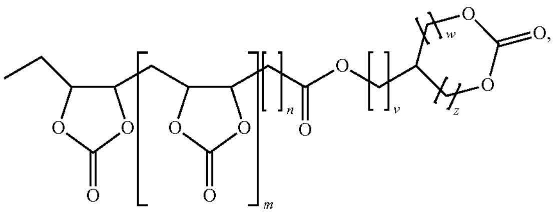

where n is between 0 and 20, inclusively, m may be between 0 and 20, inclusively, v may be between 0 and 10, inclusively, w may be between 0 and 3, inclusively, and z may be between 0 and 3, inclusively.

In some embodiments of the present disclosure, the structure may be defined by at least one of

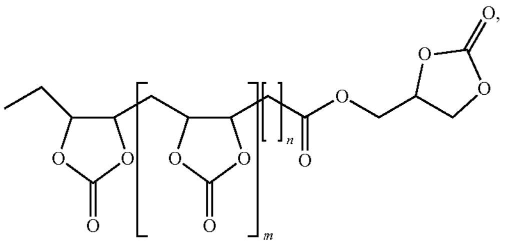

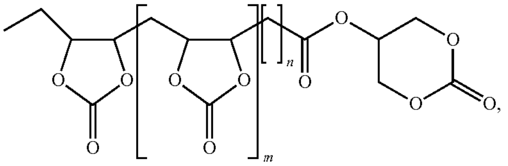

and/or

-continued

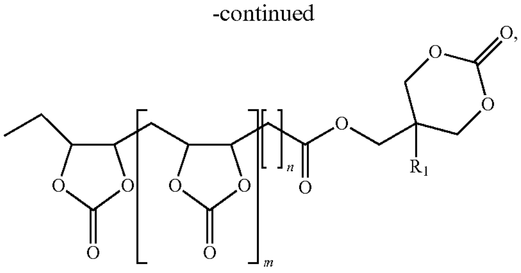

where $R_1$ includes at least one of carbon, hydrogen, or oxygen.

In some embodiments of the present disclosure, the structure may be

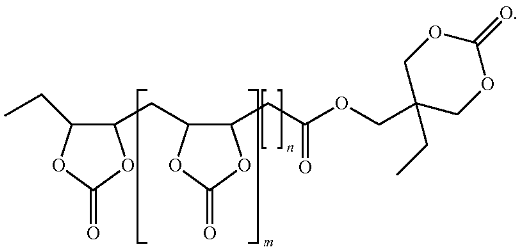

In some embodiments of the present disclosure, the structure may be defined by at least one of

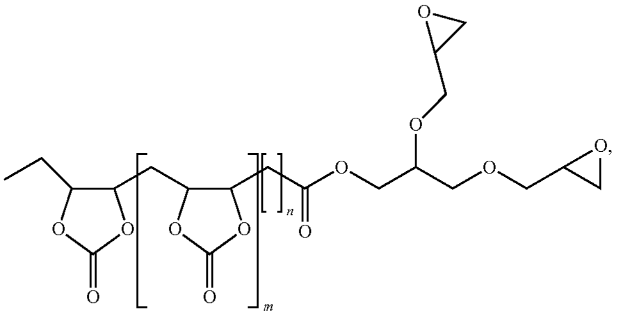

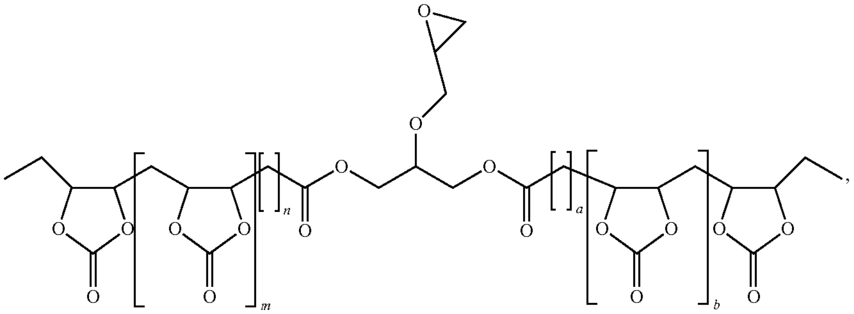

, and/or

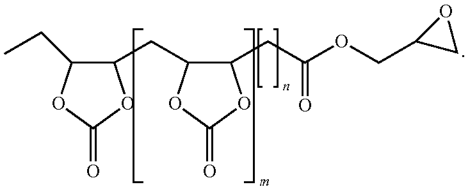

An aspect of the present disclosure is a composition that includes a structure as defined by

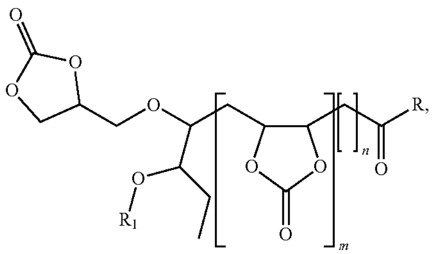

where n is between 0 and 20, inclusively, m is between 0 and 20, inclusively, R comprises at least one of carbon, hydrogen, or oxygen, and $R_1$ comprises at least one of carbon, hydrogen, or oxygen.

In some embodiments of the present disclosure, the structure may be defined by

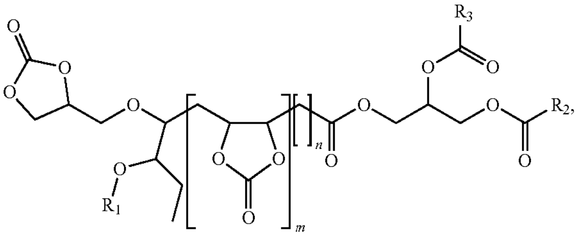

where $R_2$ includes at least one of carbon, hydrogen, and/or oxygen, and $R_3$ includes at least one of carbon, hydrogen, and/or oxygen.

An aspect of the present disclosure is a non-isocyanate polyurethane having a structure resulting from the reacting of a polyamine with a molecule having the structure

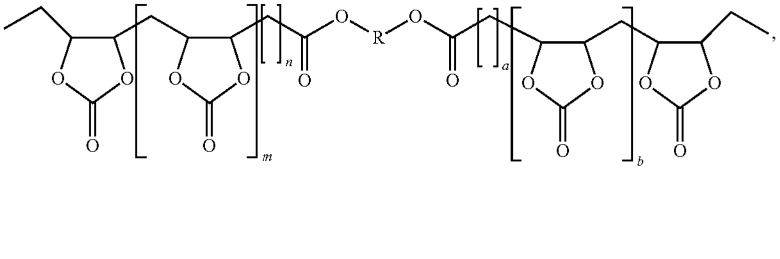

where R includes at least one of carbon, hydrogen, and/or oxygen, a is between 0 and 30, inclusively, b is between 0 and 20, inclusively, n is between 0 and 30, inclusively, and m is between 0 and 20, inclusively.

In some embodiments of the present disclosure, the non-isocyanate polyurethane may further include a Young's modulus between greater than 0 MPa and less than 1500 MPa. In some embodiments of the present disclosure, the non-isocyanate polyurethane may further include a tensile strength between greater than 0 MPa and less than 30 MPa. In some embodiments of the present disclosure, the non-isocyanate polyurethane may further include an elongation at break between greater than 0% and less than 500%. In some embodiments of the present disclosure, the non-isocyanate polyurethane may further include glass transition temperature ($T_g$) between 15° C. and 65° C.

DETAILED DESCRIPTION

Figure 1:
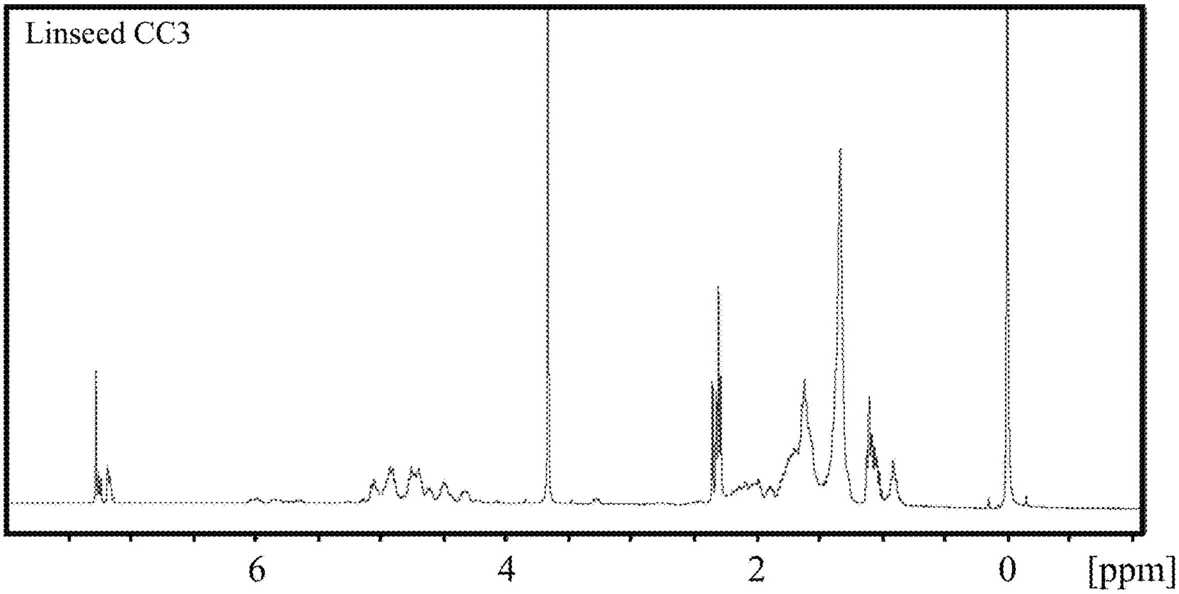
FIG. 1 illustrates NMR spectra of linseed oil derived, fatty acid methyl ester cyclic carbonate monomers, having three cyclic carbonate groups (CC3 FAME), which were subsequently reacted with diamines to produce NIPUs, according to some embodiments of the present disclosure.
Figure 2:
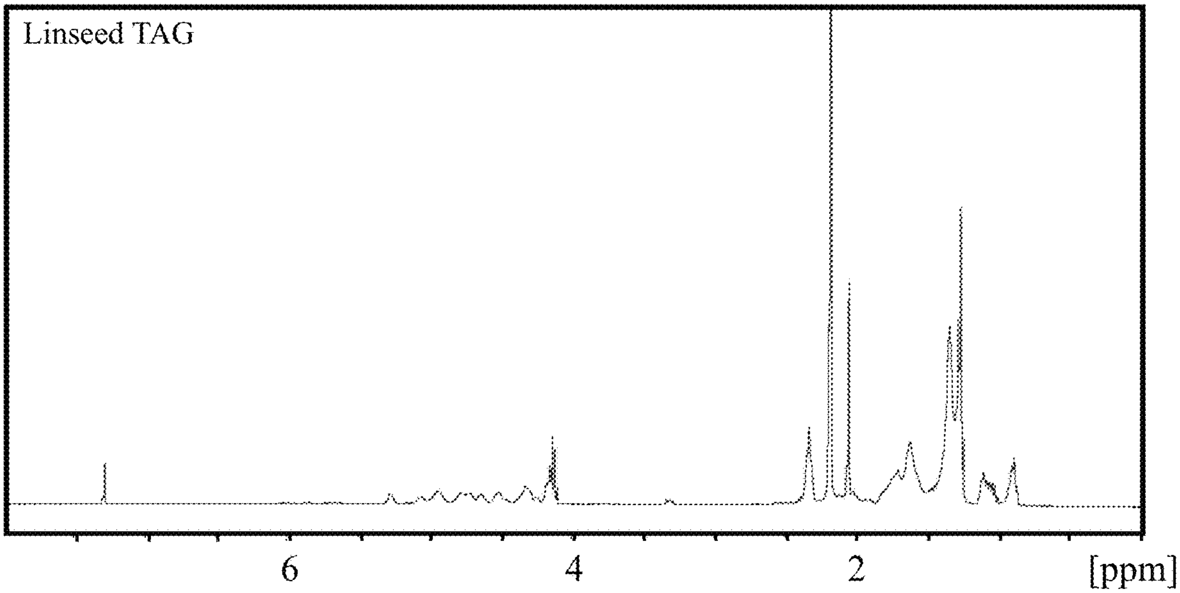
FIG. 2 illustrates NMR spectra of cyclic carbonated linseed triglyceride (linseed TAG), which were subsequently reacted with diamines to produce NIPUs, according to some embodiments of the present disclosure.
Figure 3:
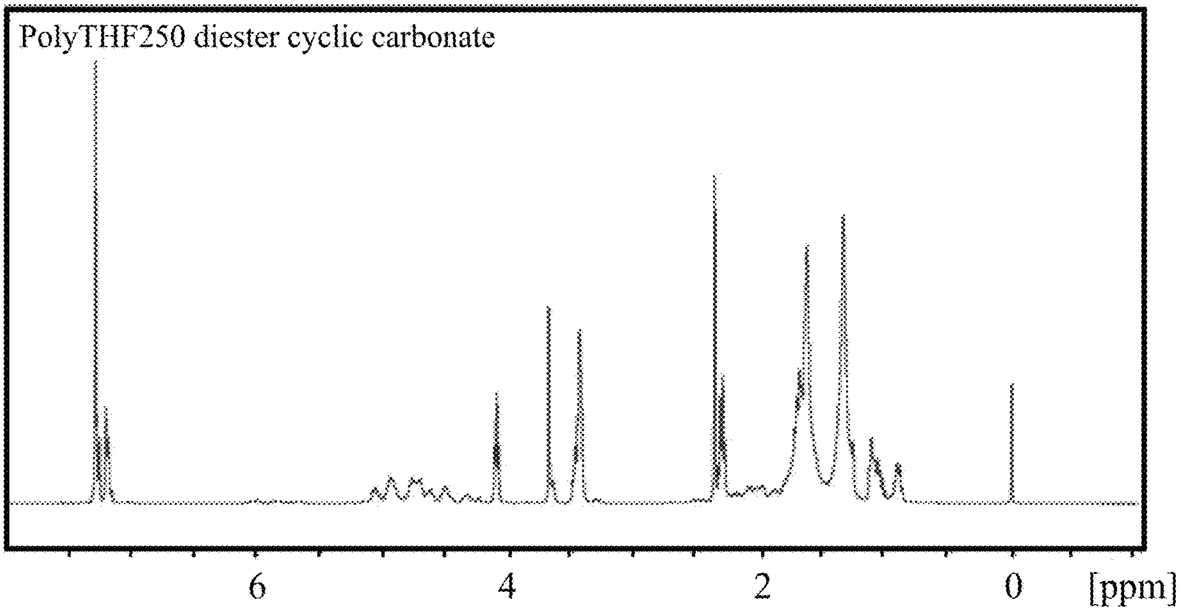
FIG. 3 illustrates NMR spectra of polyTHF250 diesters cyclic carbonates, which were subsequently reacted with diamines to produce NIPUs, according to some embodiments of the present disclosure.
Figure 4:
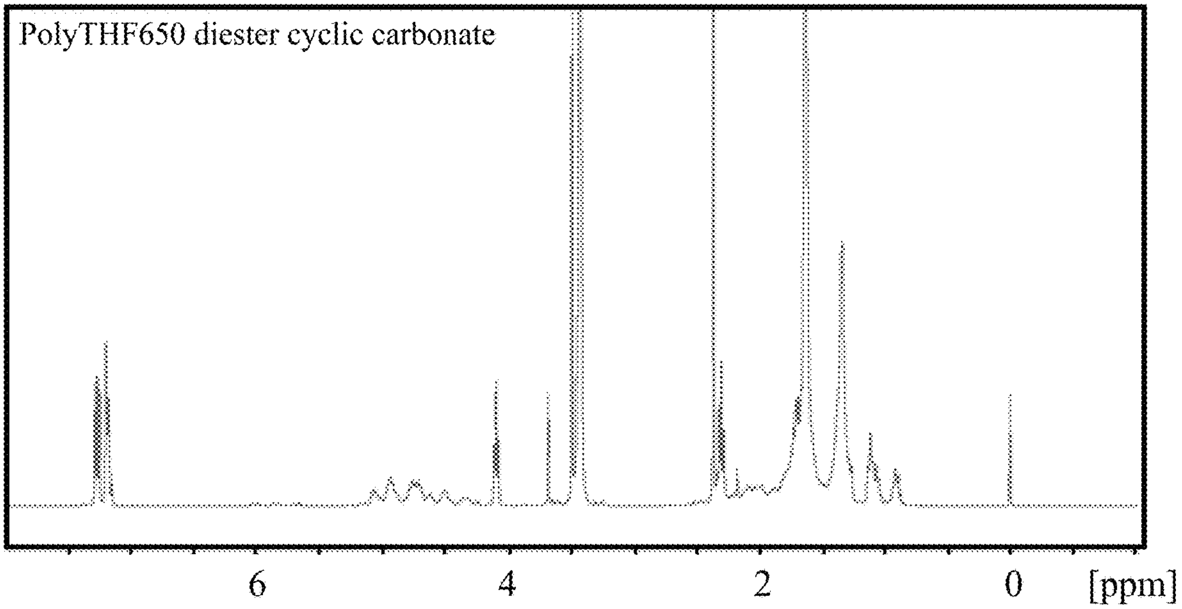
FIG. 4 illustrates NMR spectra of polyTHF650 diesters cyclic carbonates, which were subsequently reacted with diamines to produce NIPUs, according to some embodiments of the present disclosure.
Figure 5:
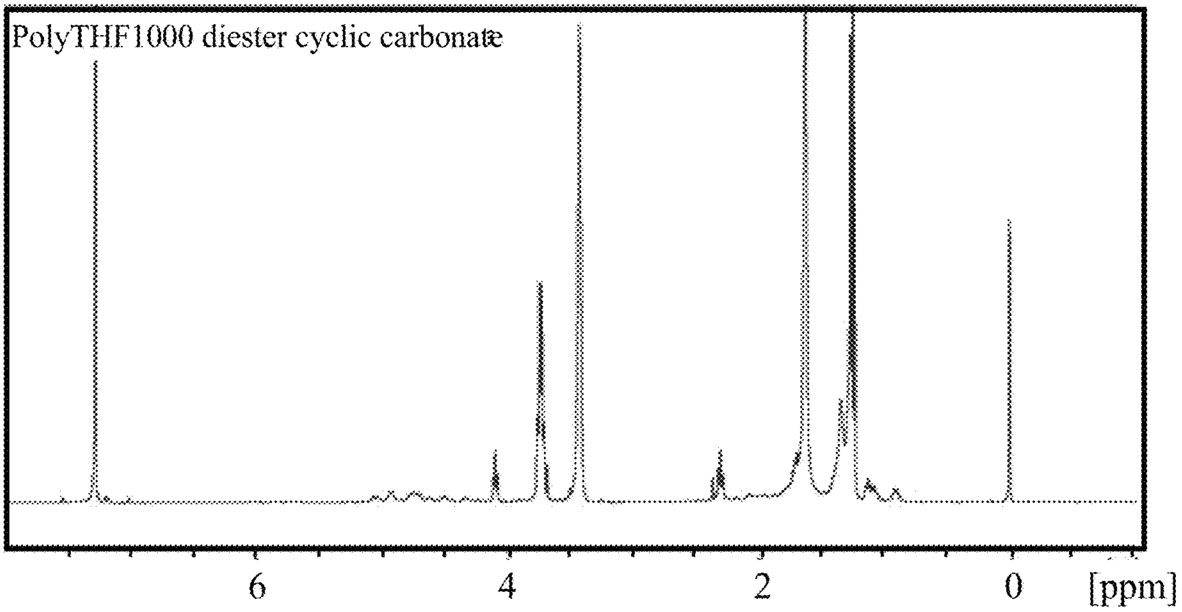
FIG. 5 illustrates NMR spectra of polyTHF1000 diesters cyclic carbonates, which were subsequently reacted with diamines to produce NIPUs, according to some embodiments of the present disclosure.
Figure 6:
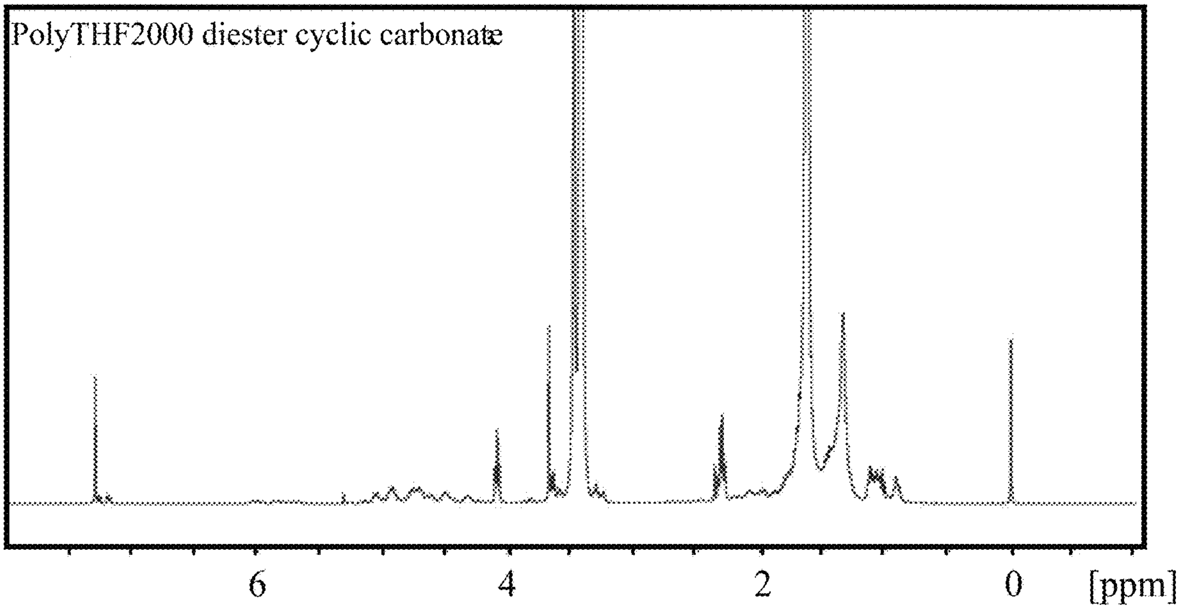
FIG. 6 illustrates NMR spectra of polyTHF2000 diesters cyclic carbonates, which were subsequently reacted with diamines to produce NIPUs, according to some embodiments of the present disclosure.
Figure 7:
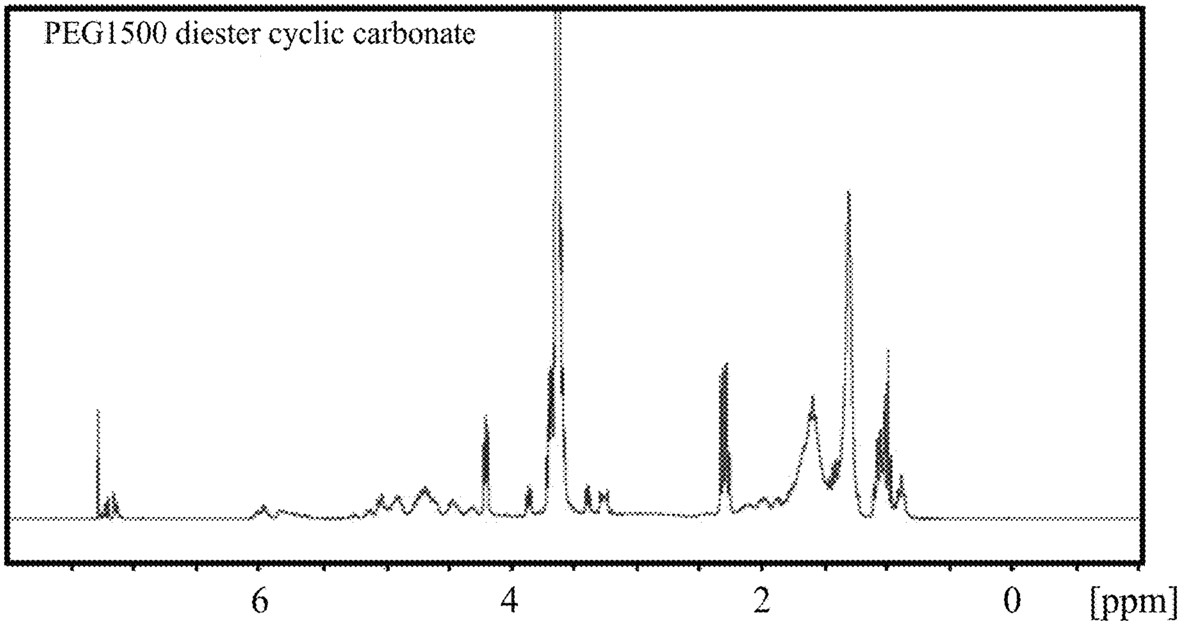
FIG. 7 illustrates NMR spectra of PEG1500 diesters cyclic carbonates, which were subsequently reacted with diamines to produce NIPUs, according to some embodiments of the present disclosure.
Figure 8:
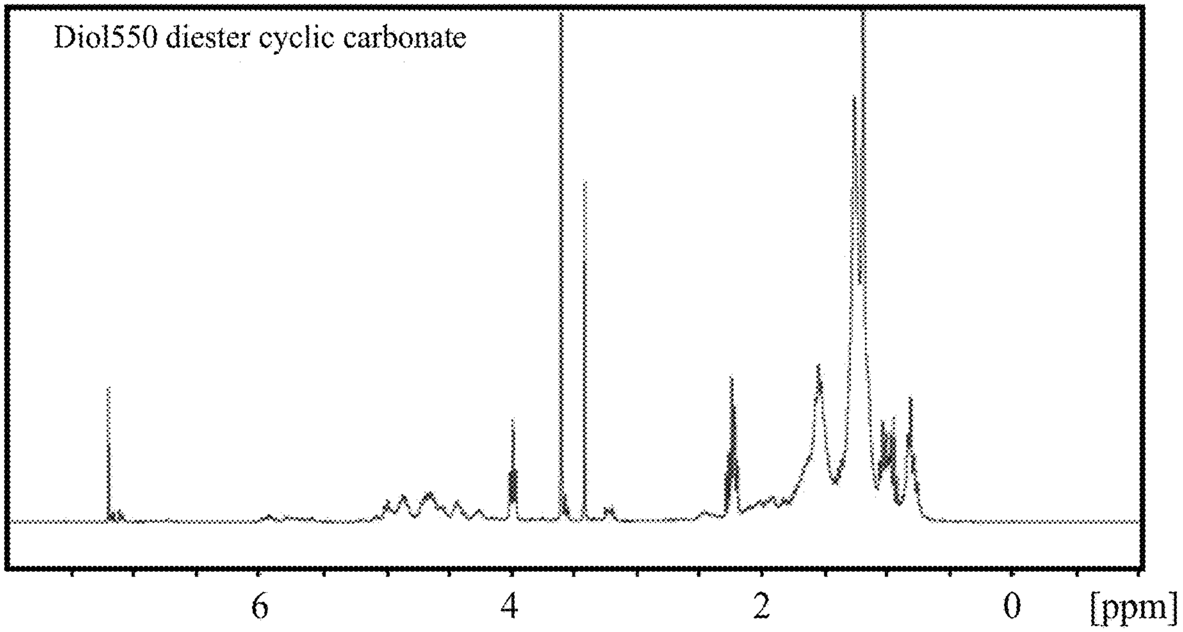
FIG. 8 illustrates NMR spectra of Diol550 diesters cyclic carbonates, which were subsequently reacted with diamines to produce NIPUs, according to some embodiments of the present disclosure.

Among other things, the present disclosure relates to fatty acid derived, cyclic carbonate-containing monomers, which are uniquely suited for the manufacture of non-isocyanate polyurethanes (NIPUs). As described herein, in some embodiments of the present disclosure, the properties of NIPUs may be tuned by changing the linking groups (e.g., diols) to produce a series of NIPU having a broad range of physical properties and/or performance metrics. In some embodiments of the present disclosure, cyclic carbonate-containing monomers may be synthesized by the transesterification of a fatty acid with a diol. Examples of fatty acids include linoleic acid, linolenic acid, eicosapentaenoic acid, docosahexaenoic acid, and linseed oil. Examples of diols include butane diol, hexane diol, polyethylene glycols (PEGs), polytrimethylene ether glycol (PO3G), polytetrahydrofurans (PTHFs), polycarbonate diols. In some embodiments of the present disclosure, a diamine may be reacted with a fatty acid to make cyclic carbonate-containing monomers. In some embodiments of the present disclosure, a fatty acid may be reacted with at least one of a diol and/or a diamine to produce cyclic carbonate-containing monomers. The basic structures of a PEG, a PTHF, and Pripol™ 2033 (i.e., Diol550) are shown below in Structures 1, 2, and 3, respectively.

Structure 1

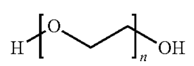

Structure 2

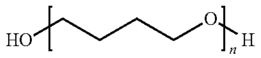

Structure 3

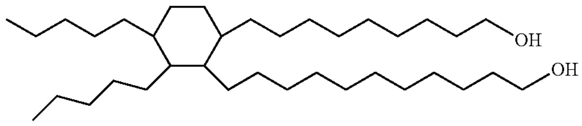

Note that when n equals 1 for Structure 1 and Structure 2, the diols are ethane diol and butane diol, respectively. In some embodiments of the present disclosure, a diol may be a straight-chained hydrocarbon, having between 1 and 18 carbon atoms, terminating on both ends with hydroxyl groups. For the example of PEGs (Structure 1), n may vary between 1 and 500. For the example PTHFs, (Structure 2) n may vary between 1 and 100. Referring to Structure 3, Pripol™ 2033 comprises a mixture of various molecules of which the one illustrated is just one example. So, Structure 3, will be referred to herein as a molecule that is always present when using Pripol™ 2033 as a diol for producing cyclic carbonate-containing monomers.

Table 1 below summarizes other specific industrially available PTHFs and other diols suitable for the reactions described herein to produce cyclic carbonate-containing monomers.

TABLE 1

Diols for Reacting with Linseed CC3

| Chemical name | Product name | Supplier | Structures |
|---|---|---|---|
| Polytetrahydrofuran 250 | PolyTHF250 | Huntsman | Structure 2; Mn of ~250 |
| Polytetrahydrofuran 650 | PolyTHF650 | Huntsman | Structure 2; Mn of ~650 |
| Polytetrahydrofuran 1000 | PolyTHF1000 | Huntsman | Structure 2; Mn of ~1000 |
| Polytetrahydrofuran 2000 | PolyTHF2000 | BASF | Structure 2; Mn of ~2000 |
| Polyethylene glycol 1500 | PEG1500 | Sigma-Aldrich | Structure 1; Mn of ~1500 |

TABLE 1-continued

Diols for Reacting with Linseed CC3

| Chemical name | Product name | Supplier | Structures |
|---|---|---|---|
| Diol550 | Pripol ™ 2033 | Croda | Structure 3; Mn of 550 |

Using materials like these to produce cyclic carbonate-containing monomers, results in monomers having a much better consistency (all vegetable oils suffer from poor product consistency) and lower viscosities. Further, utilizing enriched, highly function linseed CC3 reacted with a variety of different diols provides a method for controlling the molecular weight and/or structure of the resulting cyclic carbonate-containing monomers, thereby enable providing a manufacturer with a route for controlling the physical properties and/or performance metrics of the resultant final NIPUs synthesized. Together these advantages will result in a more scalable and reliable manufacturing process for synthesizing a variety of NIPU products.

The following section summarizes experimental results obtained from the transesterification of linseed oil (linolenic acid methyl ester derived carbonate monomer with 5-membered cyclic carbonate groups abbreviated herein as "linseed CC3" or "linseed CC3 FAME" where FAME refers to "fatty acid methyl ester") with various diols to produce cyclic carbonate-containing monomers suitable for the production of NIPUs. The generalized reaction is shown below as Reaction 1.

Reaction 1

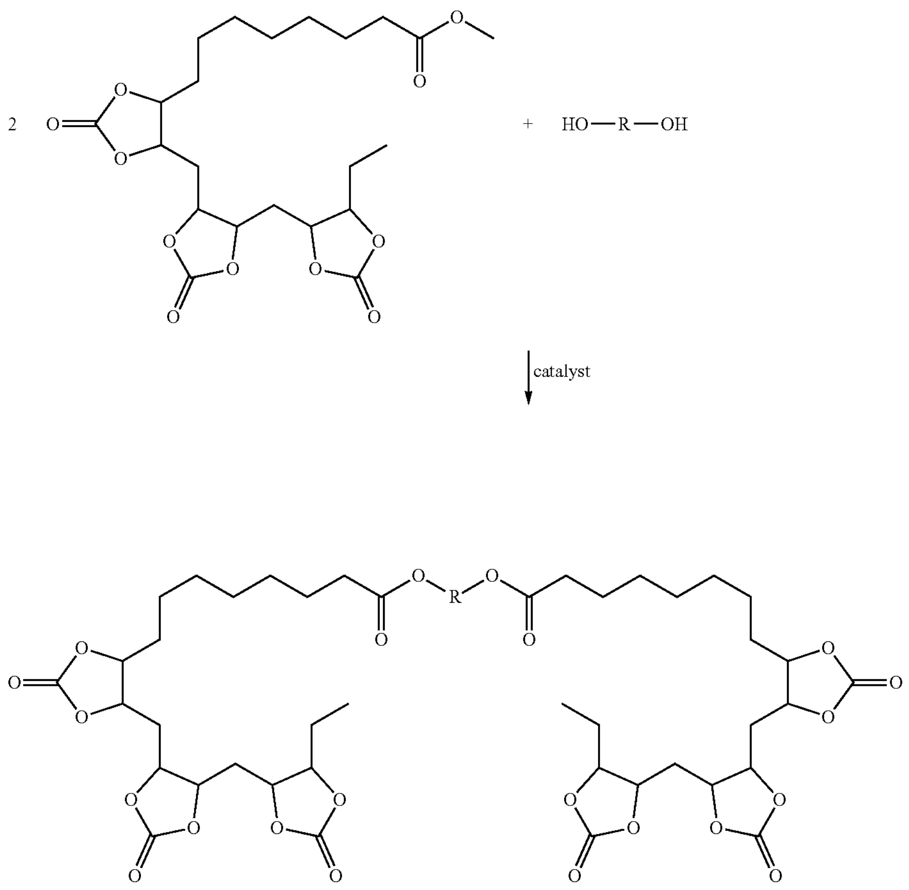

A shown in Reaction 1 and described herein, in some embodiments of the present disclosure, cyclic carbonate-containing monomers were synthesized by the transesterification of linseed CC3 with diols. However, other linseed oils and/or other oils may also be utilized as described herein to produce cyclic carbonate-containing monomers, such as CC5 and CC6 oils, where the number following the CC prefix indicates the number of unsaturated carbon bonds per chain, and the unsaturated carbon bonds are converted to cyclic carbonate groups. The general experimental method for producing these monomers by transesterification (Reaction 1) was conducted in a 250 mL round-bottom flask. Linseed CC3 (e.g., about 0.04 mol), diol (e.g., about 0.016 mol) and a solvent (e.g., toluene and/or some other aprotic solvent such as at least one of N-methy-2-pyrrolidone, benzene, acetone, acetone, dimethylformamide, etc., 50 ml) were added to the flask. The CC3 was provided in excess to ensure that each diol molecule is coupled with two CC3 molecules. Excess CC3 can be removed by solvent extraction after the transesterification react has been completed. The lipase from *Candida antarctica* B (Lipozyme CALB) was then added to the flask to catalyze the reaction, although other catalysts may have been utilized. Then the mixture was stirred at about 60° C. for about 5 days. The volatile components, e.g., methanol, were removed daily by vacuum to reduce accumulation of methanol byproduct and force the reaction to the right by Le Chatelier's principle. Solvent, e.g., toluene, was added afterward to reduce viscosity for better mixing because some toluene was removed along with the methanol during the vacuum treating. After the reaction was completed (as determined by $^1$H NMR spectroscopy by the appearance of the proton signals associated with the synthesized ester group), the product was washed with methanol to remove unreacted linseed CC3, typically in the 20-30 mol % of the starting amount of linseed CC3. The remaining layer was then rotary evaporated to remove all remaining solvent. Structure 5 presents a generalized chemical structure of the linseed oil/diol derived cyclic carbonate-containing monomers resulting from Reaction 1 above.

With cyclic carbonate-containing monomers in hand, a series of NIPUs were synthesized by aminolysis reaction. This reaction of the cyclic carbonate groups with an amine is shown below in Reaction 2. Referring to Reaction 2, in theory, when completing this reaction, a mixture of NIPUs is produced containing each of the four structures (I-IV) illustrated. For simplicity, structure (I) will be used herein to represent such a mixture, with the understanding that each of the four structures may be included in the NIPUs produced using the cyclic carbonate-containing monomers described herein. In some embodiments of the present disclosure, NIPUs were synthesized by reacting in two steps, a first reacting which was maintained for a period between 6 hours and 24 hours, or about 12 hours at a temperature between 70° C. and 110° C. and a second reacting for an additional ~12 hours at about 110° C. in an oven. In some embodiments of the present disclosure, this second reacting may be maintained for a period between 6 and 24 hours at a temperature between 110° C. and 140° C. In general, NIPUs formed from the cyclic carbonate-containing monomers described herein may by cured at a temperature between room temperature and 110° C. The first step at 70° C. allows most of cyclic carbonate to react with the diamine, and the temperature is not high enough to initiate reacting the amine groups and ester groups. After the lower temperature 70° C. curing, most of the diamine has reacted with cyclic carbonate resulting in the forming of the urethane. Increasing the temperature to about 110° C. enables the reaction of any remaining unreacted amine and cyclic carbonate. Using this strategy minimizes the reaction between ester groups and amine. Two different diamines were used to produce the NIPUs: m-xylylenediamine (MXDA by TCI) and 4,4-diaminodicyclohexylmethane (PACM by Sigma Aldrich).

Structure 5

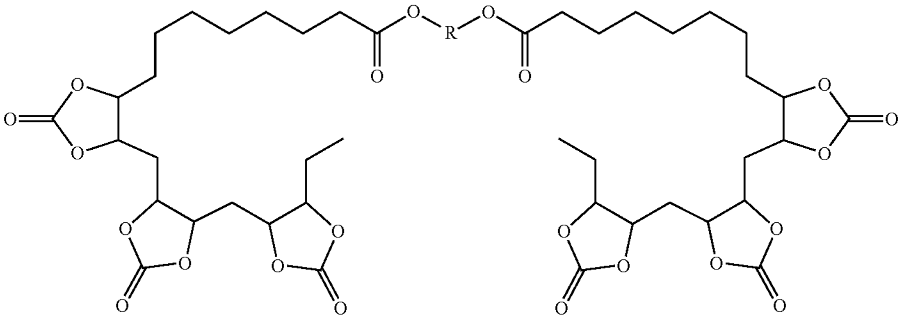

Reaction 2

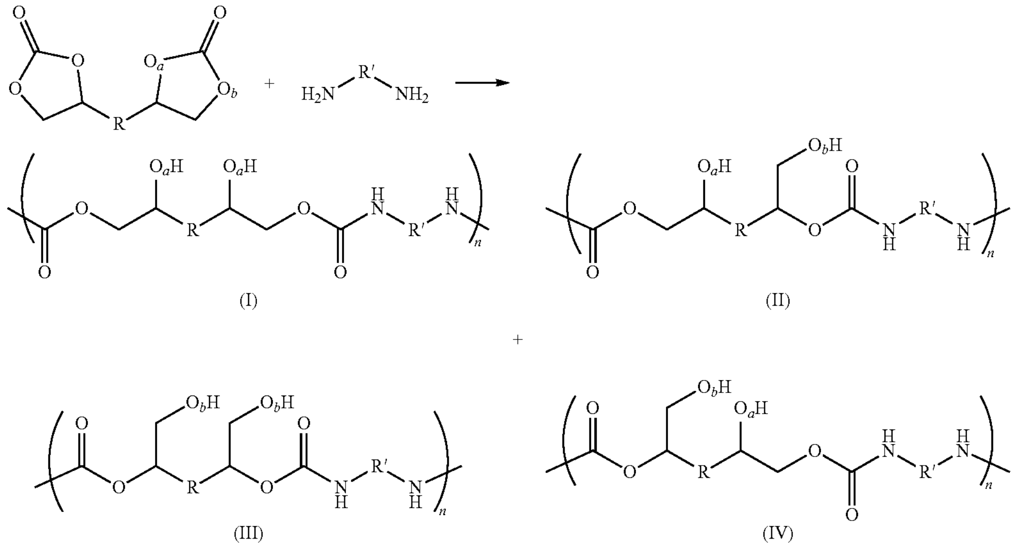

(I) (II)

+

(III) (IV)

Table 2 summarizes the linseed CC3 derived cyclic carbonate monomers tested for NIPU production as obtained by reacting two linseed CC3 molecules per diol molecule, as shown in Reaction 1 above. Table 3 summarizes the structures of diamines reacted with the cyclic carbonate monomers to produce NIPUs, and Table 4 summarizes some of the physical properties measured of the resultant NIPUs produced by Reaction 2.

TABLE 2

Linseed CC3-Derived Diesters Cyclic Carbonate Monomers

| Diester Cyclic Carbonate Product Name* | Diol Monomer Reactant | $f$ [a] | Renewable content [b] | Carbonate [c] equivalent weight | Viscosity at 70° C. (Pa · s) |
|---|---|---|---|---|---|
| DPEG 1500 | PEG 1500 | 5.6-5.8 | 100% | 250 | 0.4 |
| DTHF 250 | PolyTHF 250 | | 100% | 140 | 1.3 |
| DTHF 650 | PolyTHF 650 | | 100% | 200 | 200 |
| DTHF 1000 | PolyTHF 1000 | | 100% | 300 | 3.3 |
| DTHF 2000 | PolyTHF 2000 | | 100% | 460 | 8.4 |
| DD 550 | Pripol ™ 2033 | | 100% | 250 | 1.6 |
| Linseed TAG | NA | | 100% | 210 | 20.8 |
| Linseed CC3 FAME | NA | | 100% | 160 | 0.7 |

*General structure as shown in Structure 5.
[a] Carbonate functionality as in average number of cyclic carbonate functional groups per molecule.
[b] Renewable content was calculated by (number of renewable carbons)/(number of total carbons).
[c] Carboante equivalent weight = Mw of the cyclic carboante monomer/functionality of cyclic carboante (e.g., 2.8 CC per molecule).

TABLE 3

Exemplary Diamines

| # | Name | Structure |
|---|---|---|
| DA#1 | m-xylylenediamine (MXDA) | 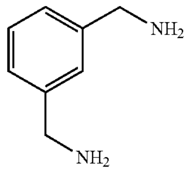 |

TABLE 3-continued

| Exemplary Diamines | | |
|---|---|---|
| # | Name | Structure |
| DA#2 | 4,4-diaminodicyclo-hexylmethane (PACM) | 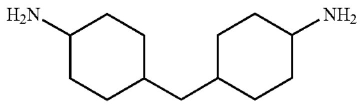 [SMILES: NC1CCC(CC2CCC(N)CC2)CC1] |

TABLE 4

NIPUs Derived from Reacting Linseed CC3-Derived Diester Cyclic Carbonates with Diamines

| Diester Carbonate | Amine | Conversion | Young's modulus (MPa) | Tensile strength (MPa) | Elongation at break (%) | $T_g$ (° C.) | Toughness (MPa) | $T_{d10\%}$ (° C.) |
|---|---|---|---|---|---|---|---|---|
| DPEG 1500 | MXDA | 87% | 1.3 | 0.4 | 51 | NA | NA | NA |
| DTHF 250 | MXDA | 89% | 1499 | 23 | 0.1 | NA | NA | NA |
| DTHF 650 | MXDA | 81% | 42 | 6.2 | 123 | NA | NA | NA |
| DTHF 1000 | MXDA | 89% | 0.4 | 0.5 | 232 | NA | NA | NA |
| DD 550 | MXDA | 93% | 242 | 4 | 32 | NA | NA | NA |
| Linseed TAG | PACM | NA | 481 ± 122 | 29 ± 6.5 | 10 ± 1 | 63 | 1.7 ± 0.5 | 293 |
| Linseed CC3 | PACM | NA | a | a | a | 52 | a | 259 |
| DTHF 250 | PACM | NA | a | a | a | 39 | a | 266 |
| DPEG 1500 | PACM | 91% | 3.6 ± 0.1 | 1.2 ± 0.2 | 447 ± 15 | −52, 35 [c] | 3.2 ± 0.4 | 294 |
| DTHF 650 | PACM | 85% | 425 ± 104 | 22.8 ± 7.4 | 16 ± 12 | 25 | 5 ± 3.6 | 282 |
| DTHF 1000 | PACM | 89% | 201 ± 75 | 9.9 ± 3.6 | 274 ± 61 | 17 | 22.9 ± 2.7 | 294 |
| DTHF 2000 | PACM | 93% | 398 ± 62 | 8.9 ± 1.3 | 6 ± 0 | b | 0.3 ± 0.2 | 311 |
| DD 550 | PACM | 81% | 206 ± 60 | 2.7 ± 0.9 | 3 ± 1 | 52 | 0.1 ± 0 | 295 |

a. Samples were too brittle to be tested on Instron tester.
b. No glass transition temperature was detected in DSC result.
[c] Two glass transition temperatures were detected in DSC result.

In some embodiments of the present disclosure, as shown in more detail below, the cyclic carbonates of carbonate-containing monomers to be used for the synthesis of NIPUs may be five-membered cyclic carbonate rings. In some embodiments of the present disclosure, the cyclic carbonates of carbonate-containing monomers may include rings that are larger, e.g., six-membered rings and larger. Reaction 3 below illustrates one pathway for obtaining such larger carbonate rings. This is a two-step process where the first step converts glycerol to an intermediate dihydroxide, which is subsequently reacted with dimethyl carbonate (DMC) to produce the larger ringed carbonate-containing monomer.

Reaction 3

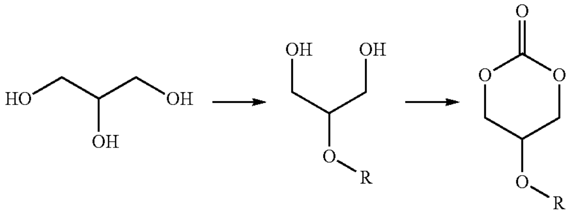

Reaction 4 and Reaction 5 illustrate specific exemplary reactions, according to some embodiments of the present disclosure. For example, one can use a C18:3 derived cyclic carbonate methyl ester to react with a glycerol using sn-2 specific lipase (see Reaction 4). Then, convert the intermediate using DMC to produce the novel compound shown below. The C18:3 derived cyclic carbonate is known to be very reactive with amine. The addition of a 6CC will further increase the reactivity of this molecule for NIPU production.

Reaction 4

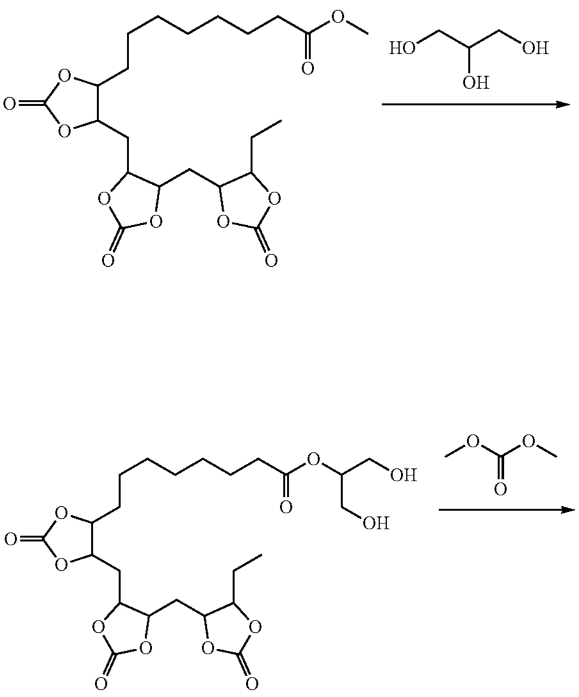

-continued

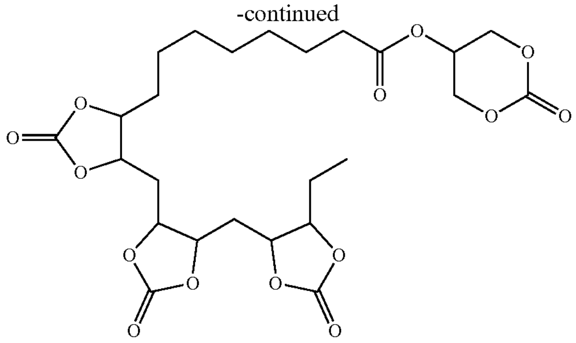

Reaction 5

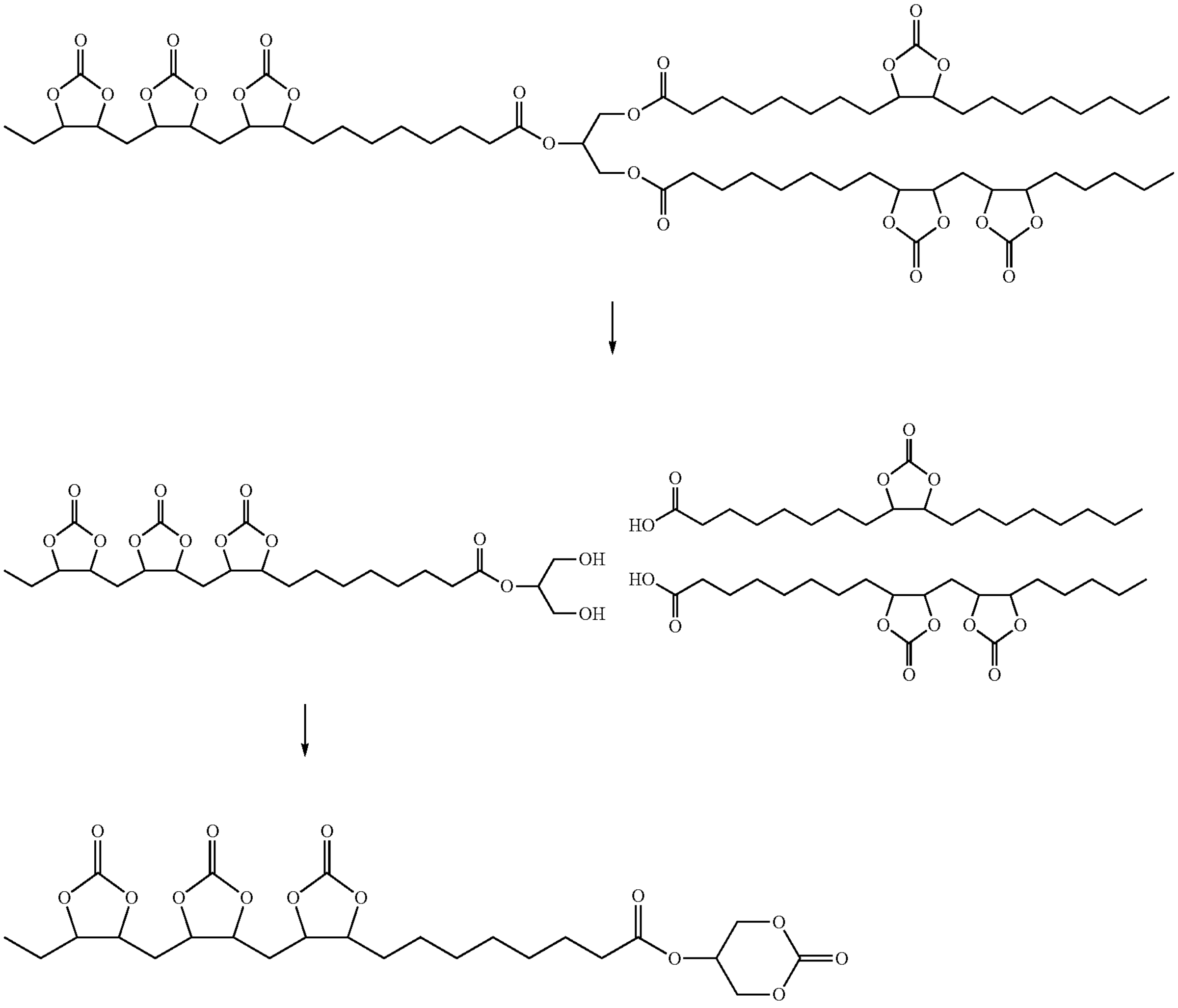

Examples of cyclic carbonate-containing monomers, according to some embodiments of the present disclosure, are illustrated below, in Scheme 1. In some embodiments of the present disclosure, a may be between 1 and 30, inclusively, b may be between 0 and 20, inclusively, m may be between 0 and 20, inclusively, n may be between 0 and 30, inclusively, x may be between 0 and 30, inclusively, and y may be between 0 and 20, inclusively.

Scheme 1. Cyclic carbonate-containing monomers for NIPU productions
(A)
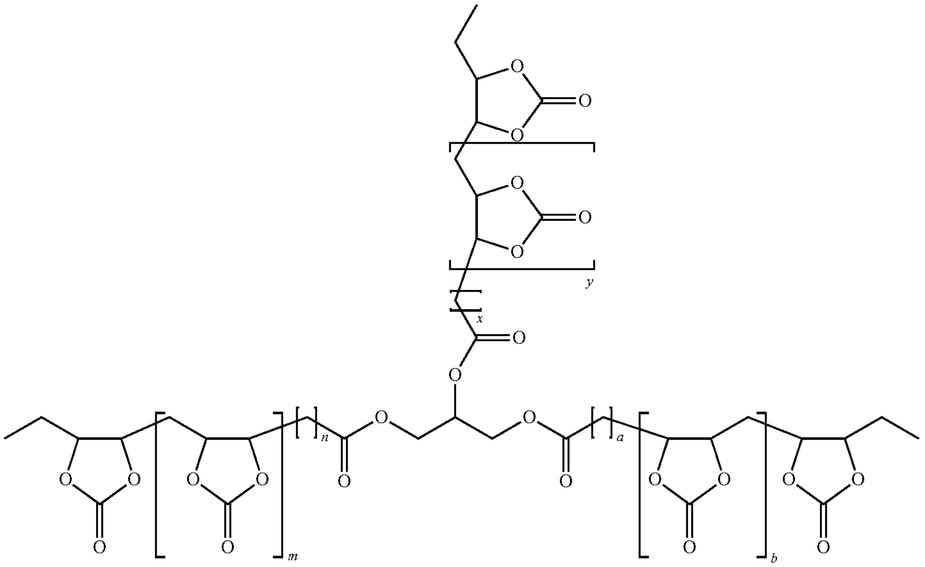
(B)
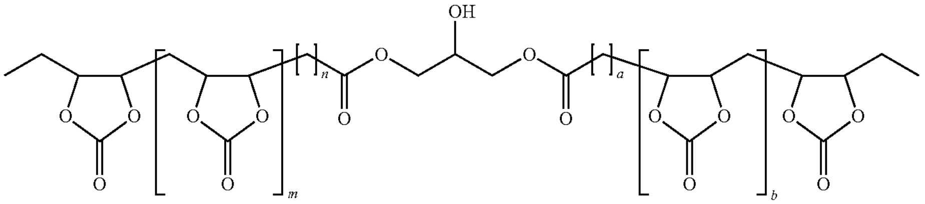
(C)
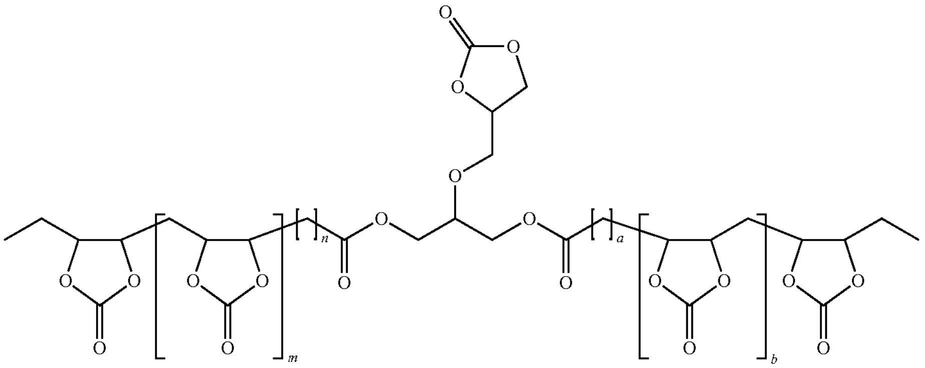
(D)
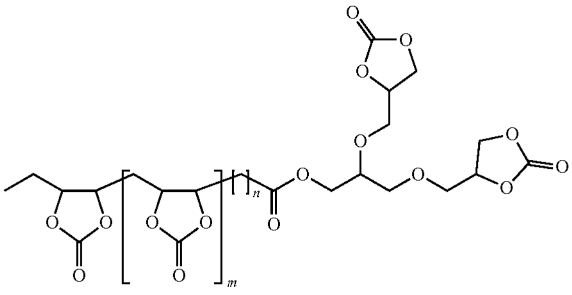
(E)
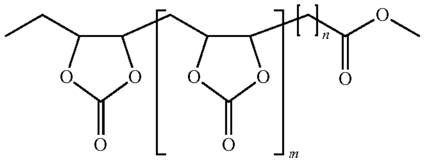

-continued (F)

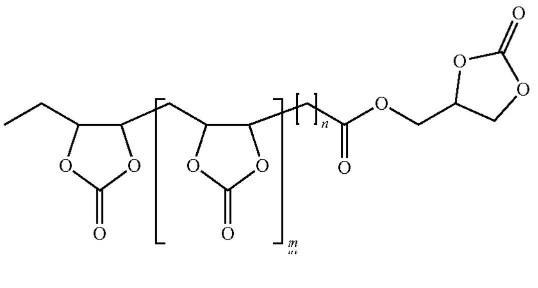

(G)

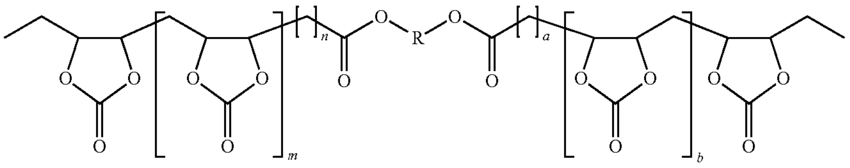

(H)

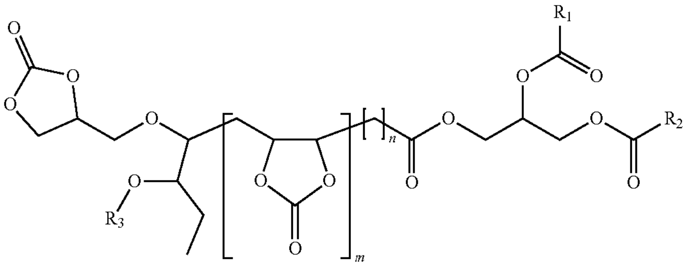

In some embodiments of the present disclosure, a cyclic carbonate-containing monomer for producing a NIPU may also include an epoxy group. For example, monomer (D) above may be synthesized in a two-step process according to Reaction 6 and Reaction 7, below:

Reaction 6

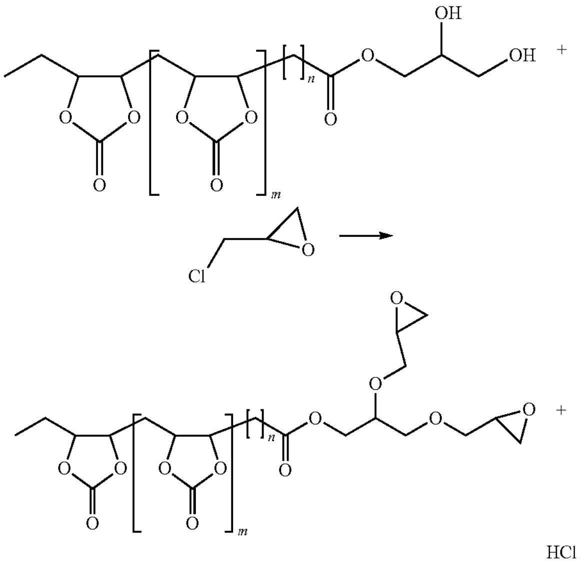

Reaction 7

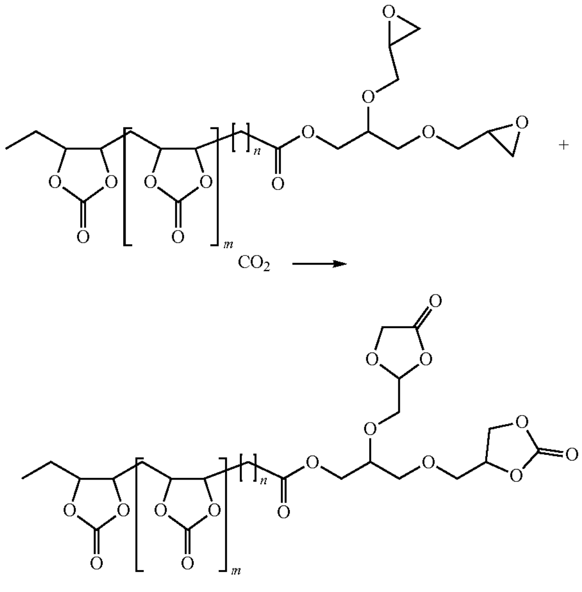

Therefore, in some embodiments of the present disclosure, hydroxyl groups on a precursor molecule may be reacted with a halogenated epoxy precursor to form the epoxidized monomer as shown in Reaction 6. Such epoxidized monomers may themselves be used directly for the synthesis of NIPUs. However, as shown in Reaction 7, in some embodiments of the present disclosure, an epoxidized monomer may be subsequently reaction with carbon dioxide to produce the cyclic carbonate-containing monomer, monomer (D) illustrated above. Similar reactions can be completed for cyclic carbonate-containing monomers (C) and (F) above, summarized below as Reactions 8-11.
Reaction 8
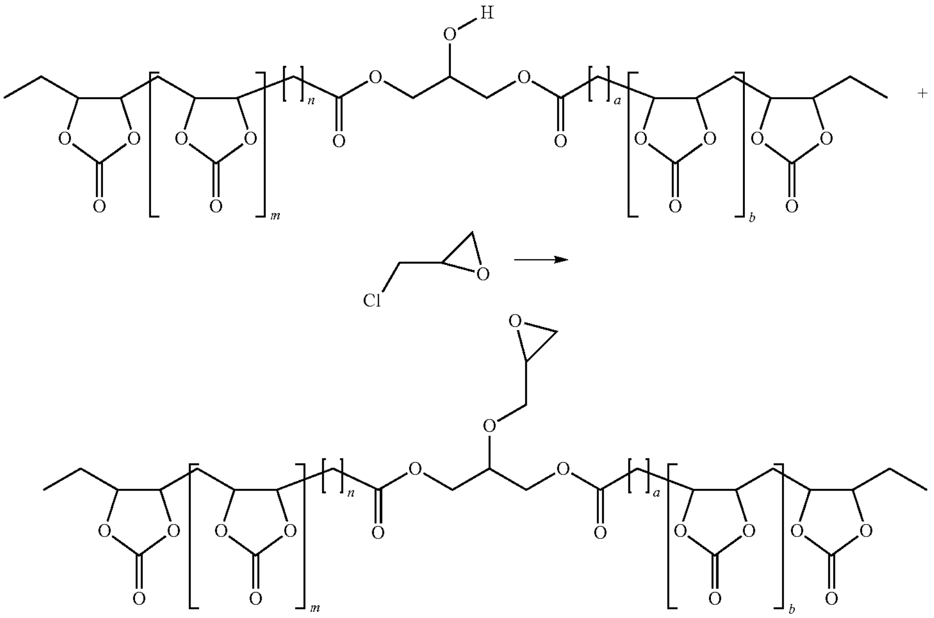
Reaction 9
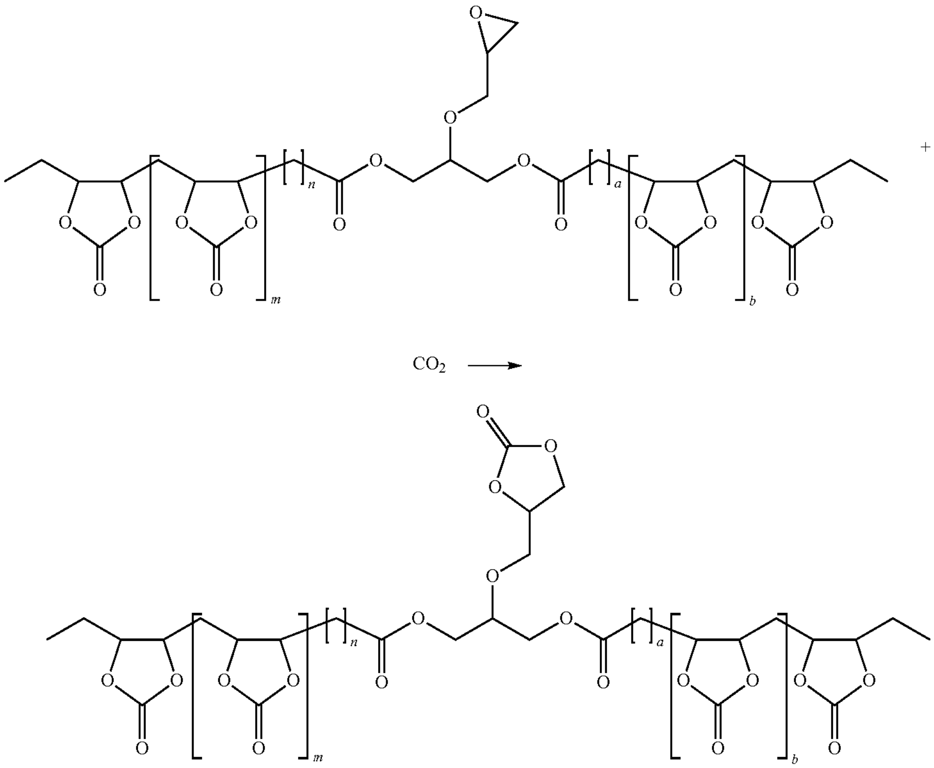

Reaction 10

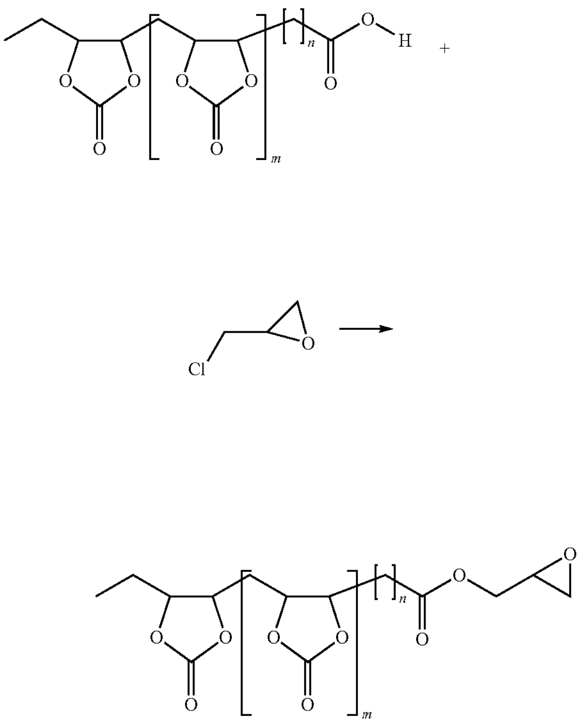

Reaction 11

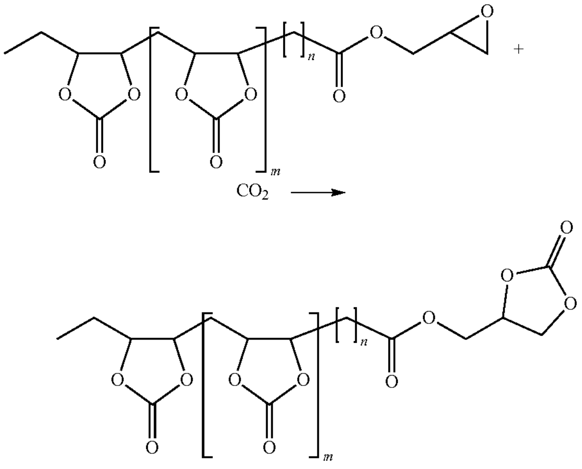

Thus, other monomers for the production of NIPUs that fall within the scope of the present disclosure include monomers having both epoxy groups and cyclic carbonate groups, with three examples shown below in Scheme 2 (monomers (I), (J), and (K)). Ranges for a, b, m, and n may be similar as those for monomers containing only cyclic carbonate groups; e.g., a may be between 1 and 30, inclusively, b may be between 0 and 20, inclusively, m may be between 0 and 20, inclusively, and n may be between 0 and 30, inclusively.

Scheme 2. Cyclic carbonate-containing and epoxy-containing monomers for NIPU productions (I)

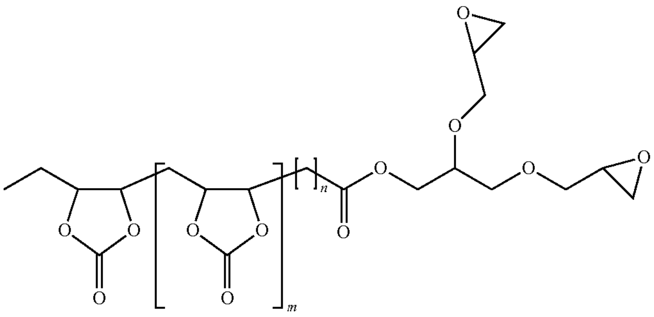

(J)

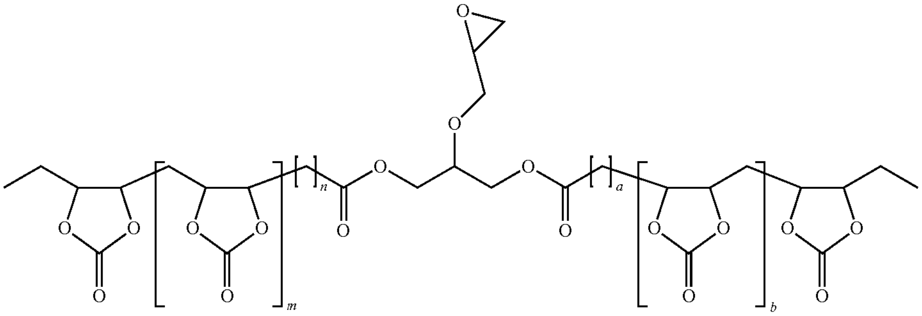

-continued (K)

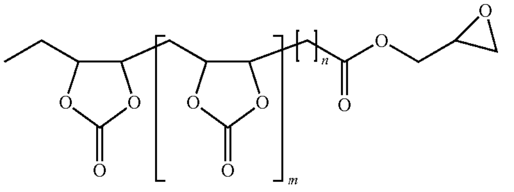

Results

Synthesis of linseed CC3 Fatty Acid Methyl Ester (FAME): Linseed CC3 FAME was synthesized through three steps: referring to Scheme 3 below, (1) transesterification of epoxidized linseed oil (ELO) to form epoxidized fatty acid methyl esters having one, two, and three epoxy groups, labeled ELO1, ELO2, and ELO3, respectively, (2) carbonation of the epoxidized FAMEs to produce cyclic-carbonate FAMEs having one, two, and three carbonate groups, labeled CC1, CC2, and CC3, respectively, and (3) purification to yield purified CC3. $^{1}$H NMR indicated that all the epoxide groups are converted to cyclic carbonate groups as shown in FIG. 1. Before purification, the linseed CC FAME contained a mixture of saturated (CC0), mono-cyclic carbonate (CC1), di-cyclic carbonate (CC2), and tri-cyclic carbonate (CC3) FAMEs. For polymer work, the goal was to enrich a fraction for the tri-cyclic carbonate FAME to maximize functionality. For this purpose, a scalable solvent separation method was developed to enrich CC3 based on the hydrophilicity imparted by each carbonate group. This was predicted by partition coefficient calculated by Marvin-Sketch: CC3 (4.50), CC2 (5.45), CC1 (6.41), and CC0 (7.29). The enhanced hydrophilicity of the CC3 FAME fraction was exploited by extracting the more hydrophobic components into hexane, leaving an enriched fraction consisting prominently of CC3 FAMEs with some CC2 FAMEs in the toluene phase. After repeated extractions, we generated a CC3 FAME fraction sufficiently enriched for CC3 diesters synthesis, the next step in our experimental plan.

Scheme 3. Synthesis of linseed CC3 FAME.
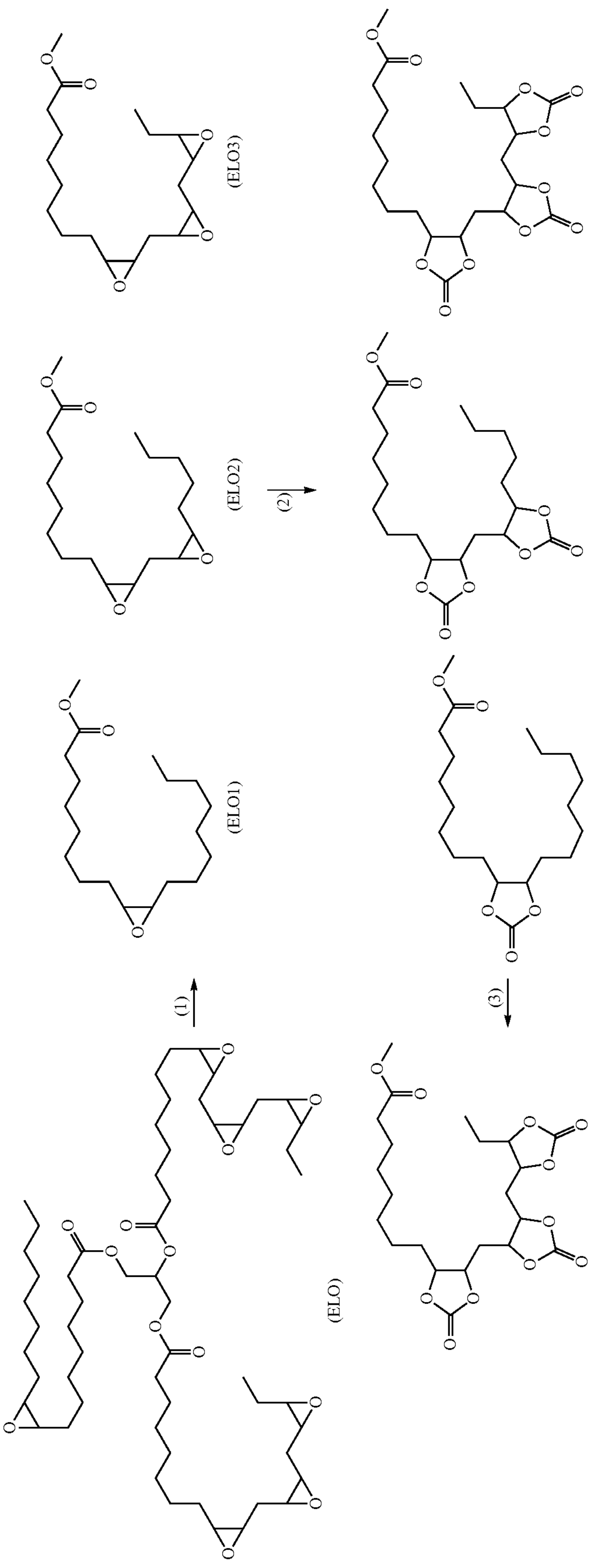
(ELO)
(ELO1)
(ELO2)
(ELO3)
(CC1)
(CC2)
(CC3)
(CC3)

Synthesis of CC3-derived diesters: Linseed oil based cyclic carbonates are low cost and having a high cyclic carbonate functionality, provide a useful starting point for biobased NIPUs. Linseed TAG, synthesized through epoxidation and carbonation was set as the baseline. The high viscosity of this feedstock (~4.5 Pa·s at 70° C.) was the primary concern for its commercial utility. In contrast, the viscosity (at 70° C.) of linseed CC3 FAME is ~0.3 Pa·s at 70° C., enabling easier industrial application process. Therefore, linseed CC3 FAME provides a low viscosity starting point for the production of a series of linseed oil based cyclic carbonates. In some embodiments of the present disclosure, this concept was expanded by generating eight linseed oil-based cyclic carbonates to be used for NIPU preparation including linseed TAG, linseed CC3 FAME, and six types of CC3-derived diesters, derived from the reaction of linseed CC3 FAME with six different diols per Reaction 1. Referring to Table 1, the six diols tested were PolyTHF250, PolyTHF650, PolyTHF1000, PolyTHF2000, PEG1500, and fatty acid dimer diol (Diol550; i.e., Pripol™ 2033). These were chosen, in part, because they offer potential for using biobased feedstocks such as commercially available polyTHF materials (BASF) and PEG materials (Sigma) to yield more sustainable polymers.

Figure 9A:
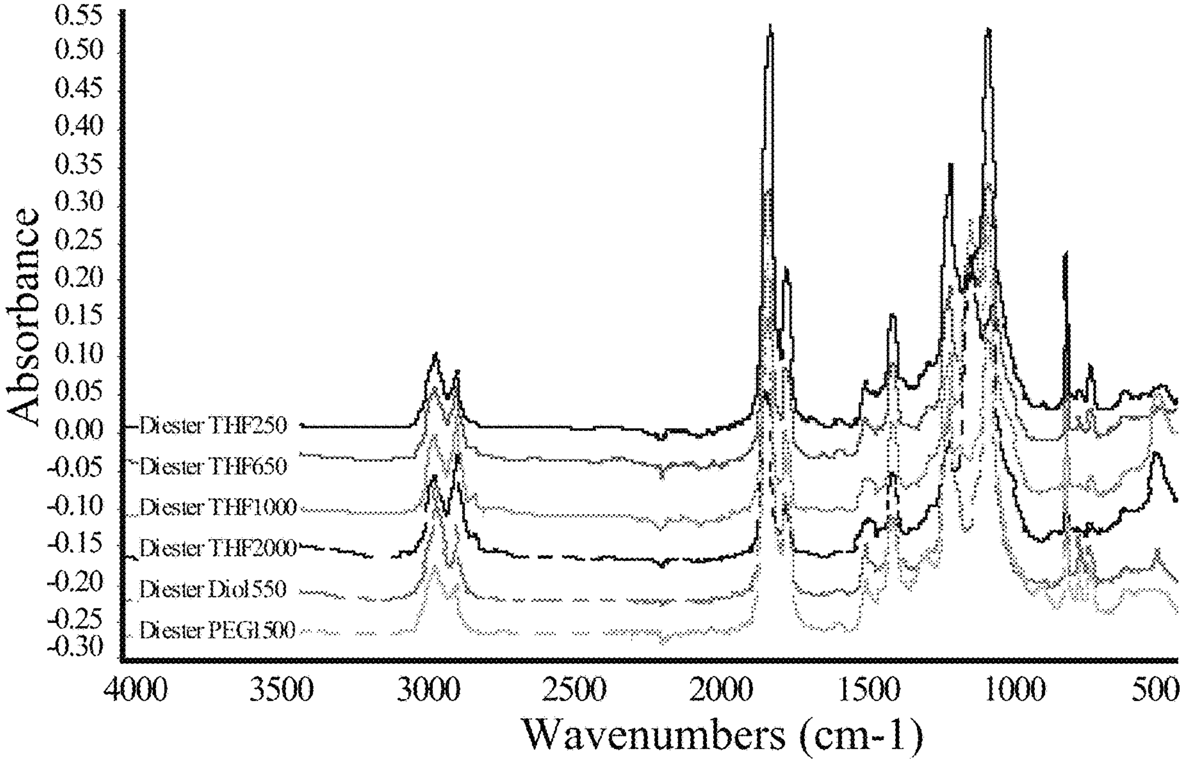
FIG. 9A illustrates FTIR spectra of diester cyclic carbonates, which were subsequently reacted with diamines to produce NIPUs, according to some embodiments of the present disclosure.
Figure 9B:
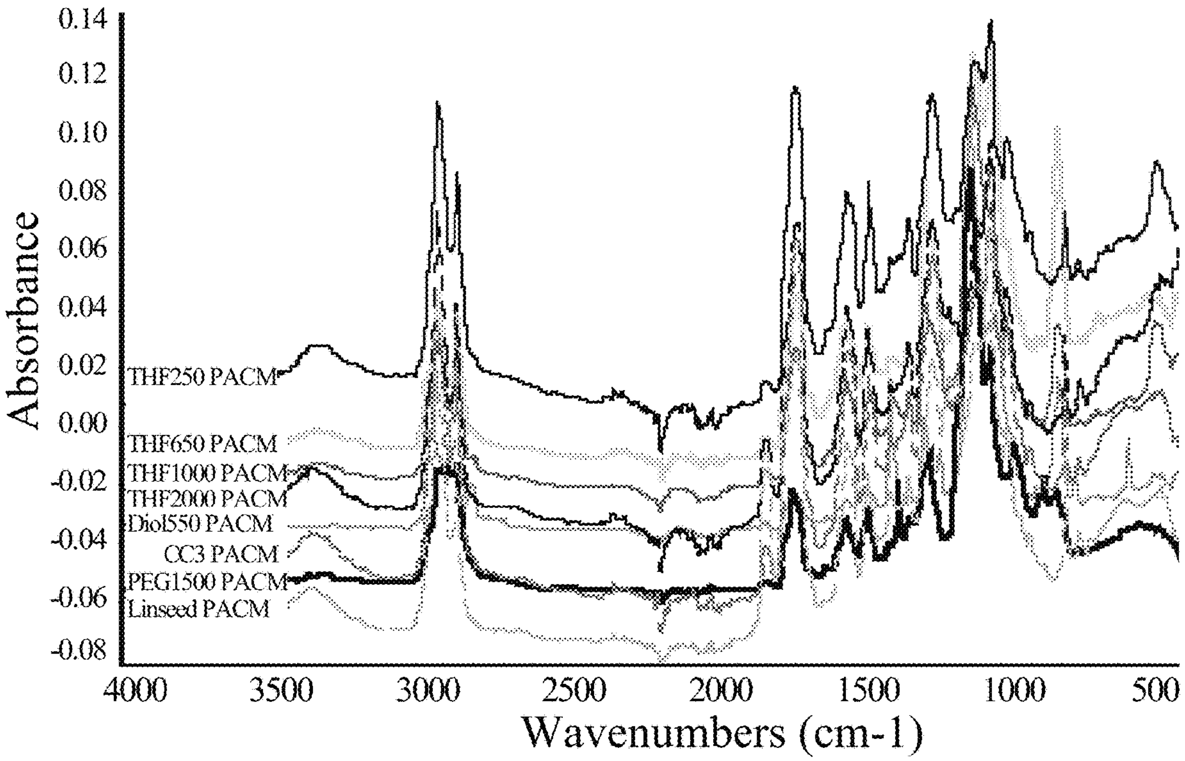
FIG. 9B illustrates FTIR spectra of the NIPUs produced from the diester cyclic carbonates illustrated in FIG. 9A, according to some embodiments of the present disclosure.

To synthesize the CC3-derived diesters, a transesterification reaction between the diols and the linseed CC3 FAME was carried out. Lipases were chosen to catalyze the reaction rather than the more standard approach using NaOH, to avoid hydrolyzing the cyclic carbonate groups. Immobilized lipase from *Candida antarctica* B (CALB) was used as catalyst since it has been widely studied and commonly used for catalyzing transesterification. From the results, FTIR and $^{1}H$ NMR confirmed the chemical structures of the CC3-derived diesters which indicated the successful transesterification and cyclic carbonate protection. The full characterization data was shown in FIGS. 1-9A/B. The clearly shown signals at 4.05 ppm in $^{1}H$ NMR indicates the formation of ester linkages between linseed CC3 FAME and diols. The strong signals of cyclic carbonate carbonyls (1800 $cm^{-1}$) are detected in FTIR (see FIG. 9A (S9)), which indicated the lipase catalyzed transesterification did not affect the cyclic carbonate group. The basic information of CC3-derived diesters is summarized in Table 2 above. The successful synthesis of CC3-derived diesters demonstrated the CALB immobilized lipase is an effective catalyst for transesterification of cyclic carbonates with methyl ester group. FIG. 9B illustrates FTIR spectra of NIPU products resulting from the reaction of the cyclic carbonate-containing monomers whose FTIR spectra are summarized in FIG. 9A. As shown in the FTIR, the cyclic carbonate peak (1800 cm-1) diminished in size, indicating the conversion of cyclic carbonate. Peaks in 1711 and 1535 cm−1 indicate the formation of urethane groups.

Figure 10:
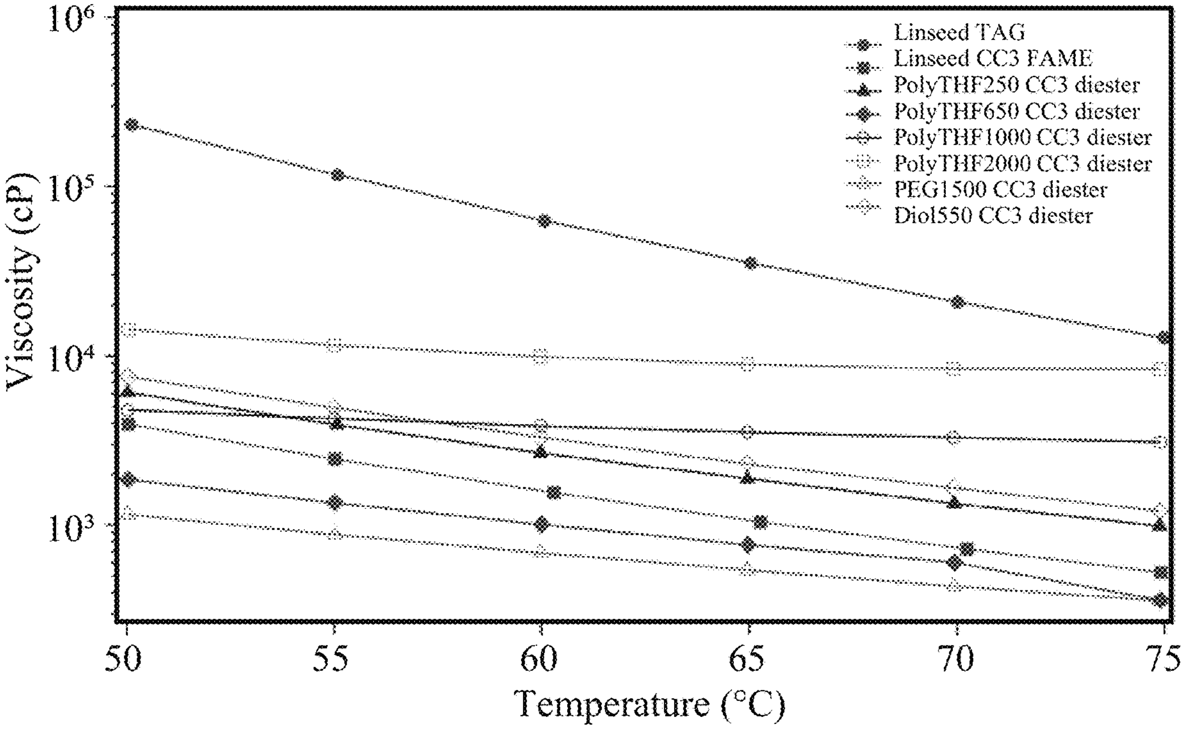
FIG. 10 illustrates viscosity vs temperature data of linseed TAG, linseed CC3 FAME, and CC3-derived diesters, according to some embodiments of the present disclosure.

FIG. 10 shows viscosity of cyclic carbonates as a function of temperature within the range of normal NIPU processing temperature. As expected, all the cyclic carbonates showed decreasing viscosity as increasing temperature. Compered to linseed TAG, all CC3-derived diesters showed dramatically lower viscosity which enables easier process and requires less energy for production. The lower viscosity of the CC3-derived diesters was possibly attributed to the less chain entanglement, relocation of adjacent ester groups, and incorporation of ether groups. Table 2 above summarizes the viscosity at 70° C. of the CC3-derived diesters.

Figure 11:
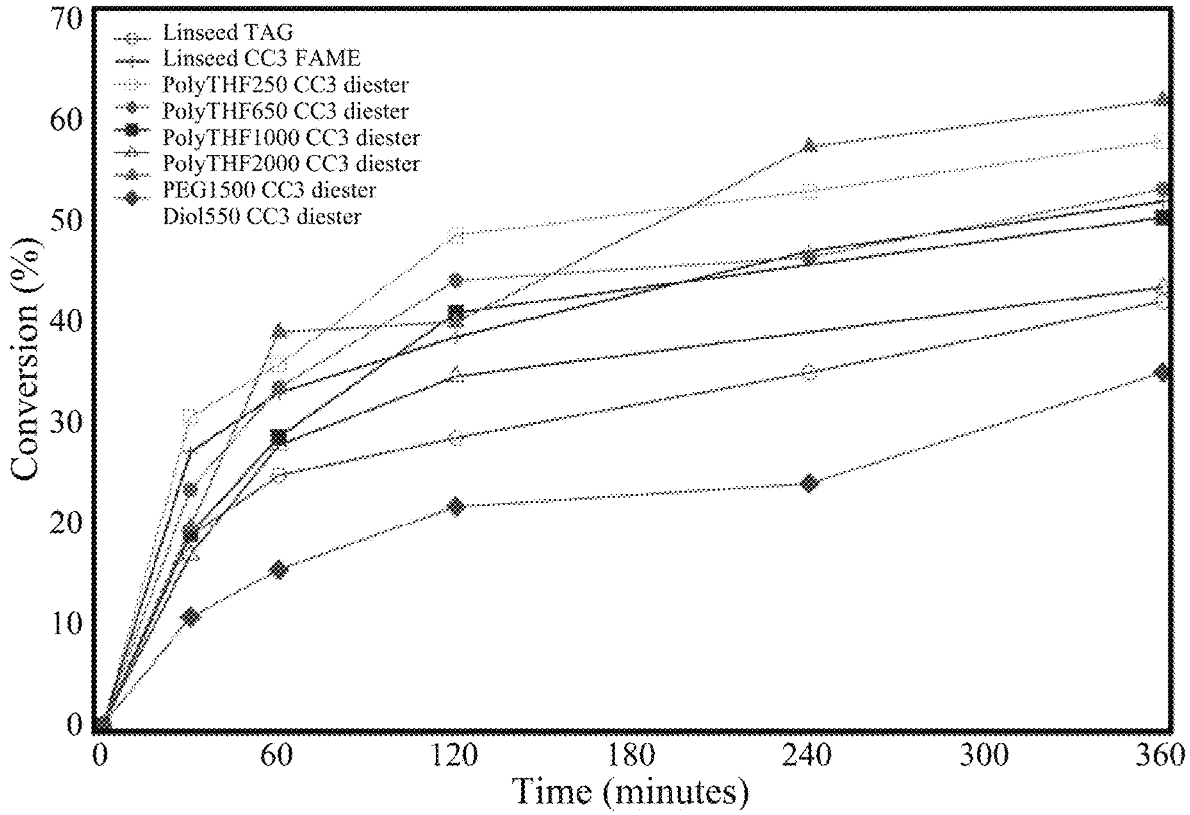
FIG. 11 illustrates conversion vs time date of PACM reacting with linseed TAG, linseed CC3 FAME, and CC3 diesters, according to some embodiments of the present disclosure.

NIPU Synthesis: For the NIPU formulations disclosed herein, PACM was chosen as the amine crosslinker. To compare aminolysis reaction rates of different CC3-derived diesters, the conversion of carbonyl group in cyclic carbonate (1800 $cm^{-1}$) was monitored by FTIR during the polymerization of cyclic carbonates and PACM. Linseed TAG, linseed CC3 FAME, and the six CC3-derived diesters were reacted with PACM at 70° C. for 6 h, separately. FIG. 11 shows the conversion change at different curing time. For control samples, linseed CC3 FAME demonstrated higher reactivity than linseed TAG due to the uniformity of cyclic carbonate group density. These results demonstrate that the reactivity towards amine of FAME cyclic carbonate followed the order of CC3>CC2>>CC1. In this work, linseed TAG contains 53% of CC3, 16% of CC2, and 21% of CC1, while linseed CC3 FAME contains 85% of CC3 and 15% of CC2. Thus, the higher cyclic carbonate group density of linseed CC3 FAME leads to a faster reaction rate. Compared to linseed TAG, most of CC3-derived diesters showed higher reaction rate because of the higher cyclic carbonate density, except Diol550 (i.e., Pripol 2033) CC3 diester. The lower reaction rate of Diol550 CC3 diester is mainly caused by the steric effect of long branched side chain in dimer acid structure. For polyTHF CC3-derived diesters, with increasing diol molecular weight, the reaction rate of the polyTHF CC3 diesters decreased. Most of CC3-derived diesters showed obviously higher reactivity than linseed TAG which saves time and energy for NIPU curing.

Figure 12:
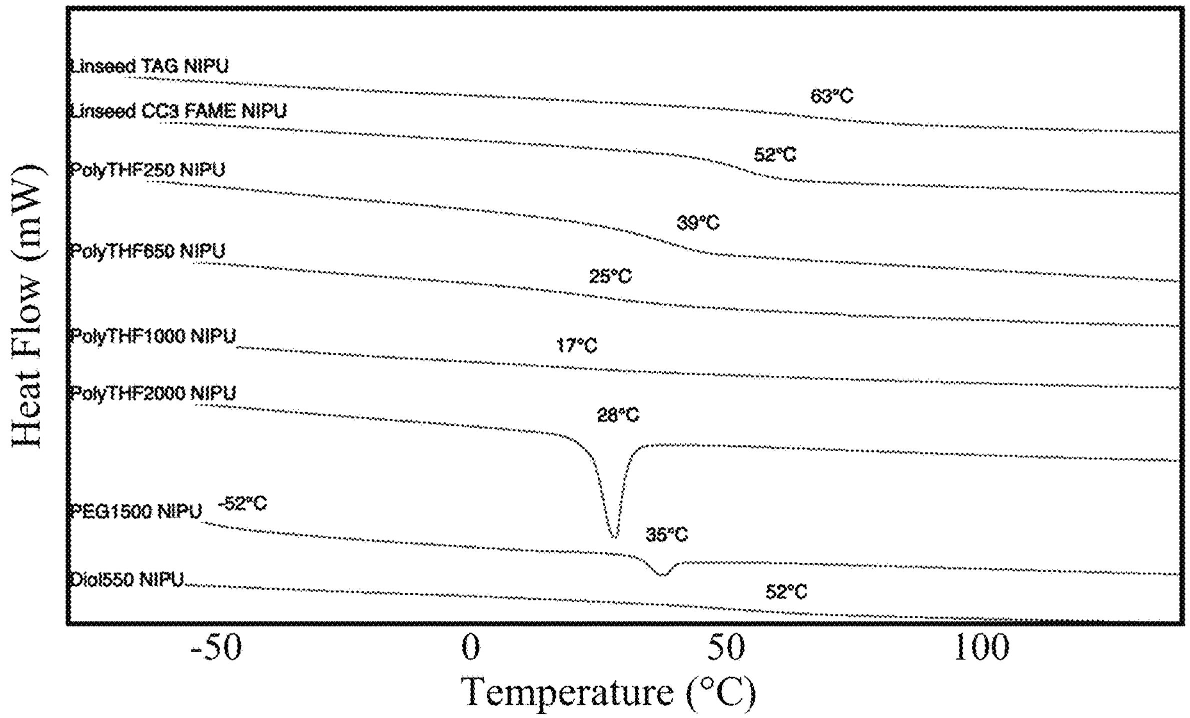
FIG. 12 illustrates DSC curves of NIPUs from the reaction of PACM with linseed TAG, linseed CC3 FAME, and CC3 diesters, according to some embodiments of the present disclosure.

Glass transition temperatures: DSC was employed to determine the $T_g$ of CC3 diesters based NIPU. The DSC curves of NIPU are showed in FIG. 12 and the $T_g$ are listed in Table 4 above. For control samples, linseed TAG NIPU showed a $T_g$ at 63° C. which is 11° C. higher than $T_g$ of linseed CC3 FAME NIPU because the triglyceride structure in linseed TAG forms NIPU with higher crosslink density. From PolyTHF250 to PolyTHF1000 NIPU, the $T_g$ decreased with increasing molecular weight of PolyTHF due to longer PolyTHF molecule chain increases the mobility of polymer segment. However, instead of $T_g$, PolyTHF2000 NIPU showed a distinct melting point of crystallization which indicated the formation of crystallization induced by PolyTHF2000 diol. By controlling the polyether chain length, PEG1500 NIPU clearly showed two glass transition temperatures caused by the microphase separation.

Figure 13:
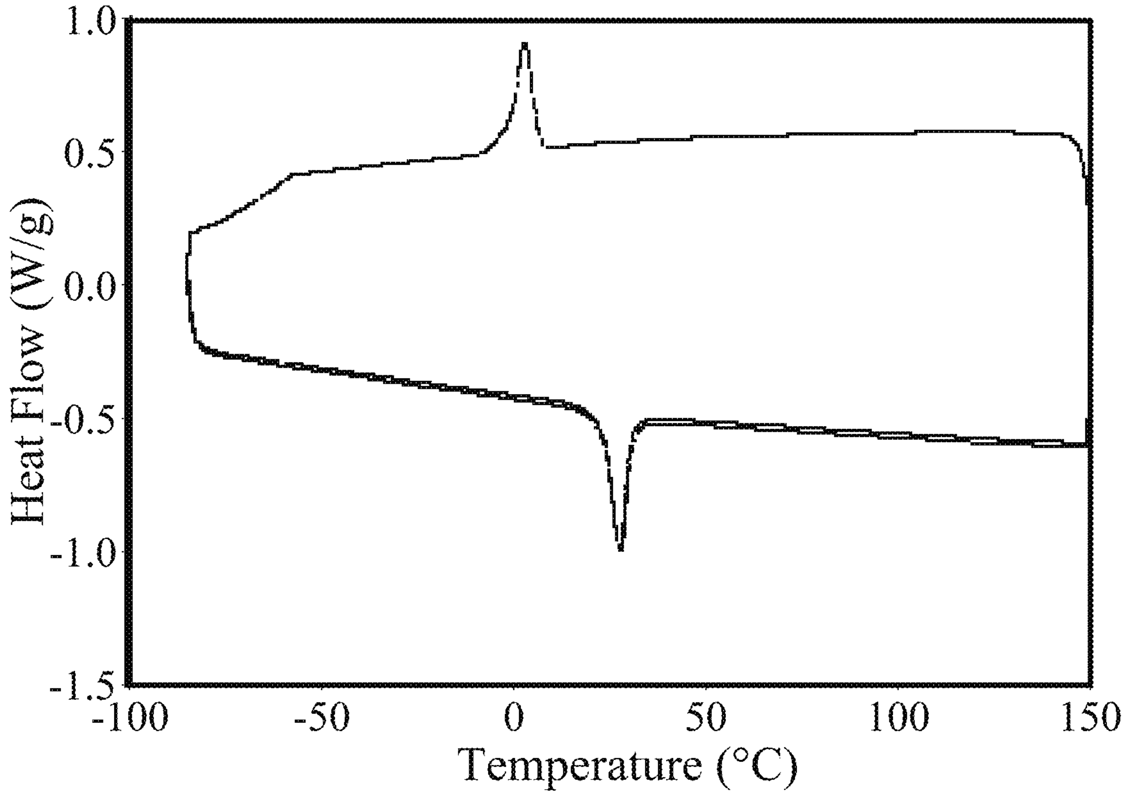
FIG. 13 illustrates DSC curves of polyTHF2000 diesters CC-PACM, according to some embodiments of the present disclosure.
Figure 14:
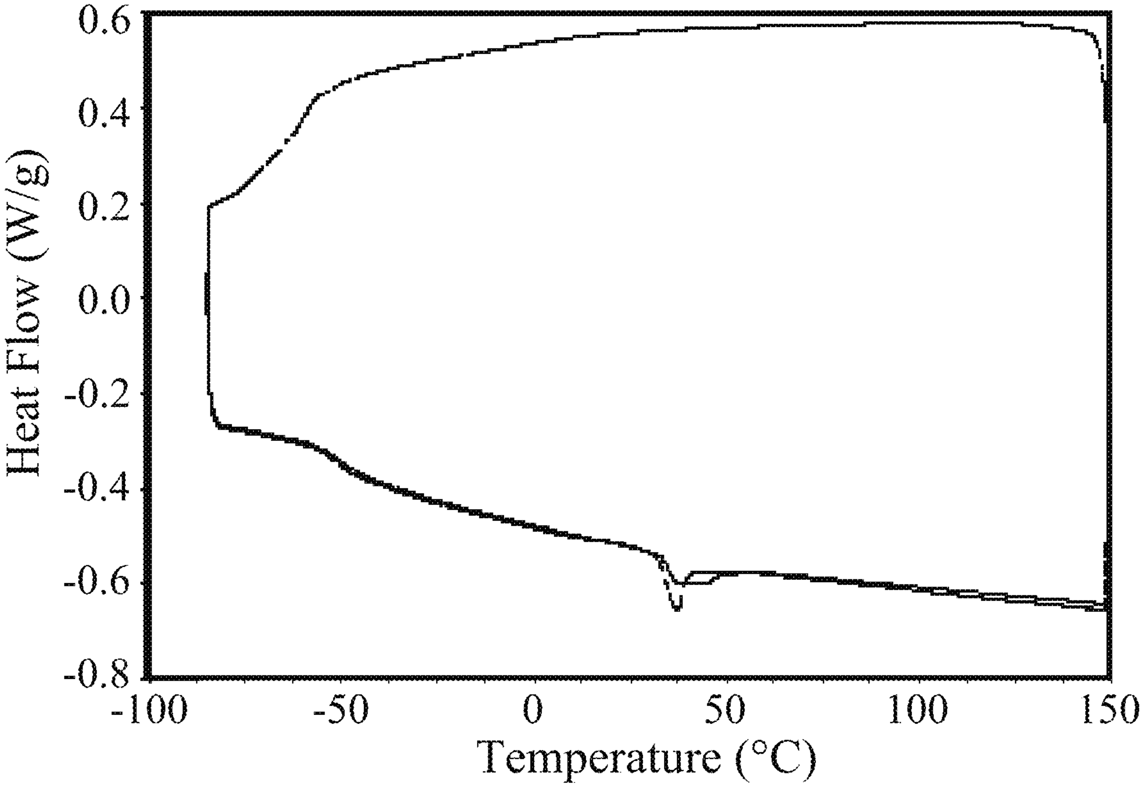
FIG. 14 illustrates DSC curves of PEG1500 diesters CC-PACM, according to some embodiments of the present disclosure.

The Diol550 NIPU exhibited one $T_g$ at 52° C. which is relatively high because the aliphatic ring in Diol550 hindered chain. Full DSC temperature cycle curves of the polyether based NIPUs are shown in FIGS. 13 and 14.

The tensile properties of CC3 diester NIPUs, including Young' modulus, tensile strength, elongation-at-break, and toughness, were evaluated as summarized in Table 4 above. As a baseline, the linseed TAG NIPU showed high modulus, strength, and low elongation and toughness. The linseed CC3 FAME NIPU and PolyTHF250 NIPUs were too brittle to be tested because the high stiffness of PACM and lack of flexible molecule chain. PACM contains two cyclohexane rings which increase the rigidity of materials. Although there is a linear polyether chain in PolyTHF250 NIPU, it is not enough to provide sufficient flexibility. For the PolyTHF650 NIPU, the flexibility slightly increased though still rigid, manifesting an elongation-at-break of 16%, with high modulus and strength. In contrast, the PolyTHF1000 NIPU exhibited excellent elastomeric features with 201 MPa modulus, 9.9 MPa strength, 274% elongation-at-break and 22.9 MPs toughness. It was interesting to observe that extending the polyether backbone further with the PolyTHF2000 NIPU resulted in an extremely low elongation (consistent with the DSC results), indicating that optimal chain length can be found. The superior tensile properties of PolyTHF1000 NIPU was predominated by the PolyTHF1000 diol introducing enough flexibility as soft segment and PACM providing rigidity as hard segment, like traditional PU. However, only one $T_g$ was detected in DSC which indicated the microphase separation is not obvious.

Figure 15:
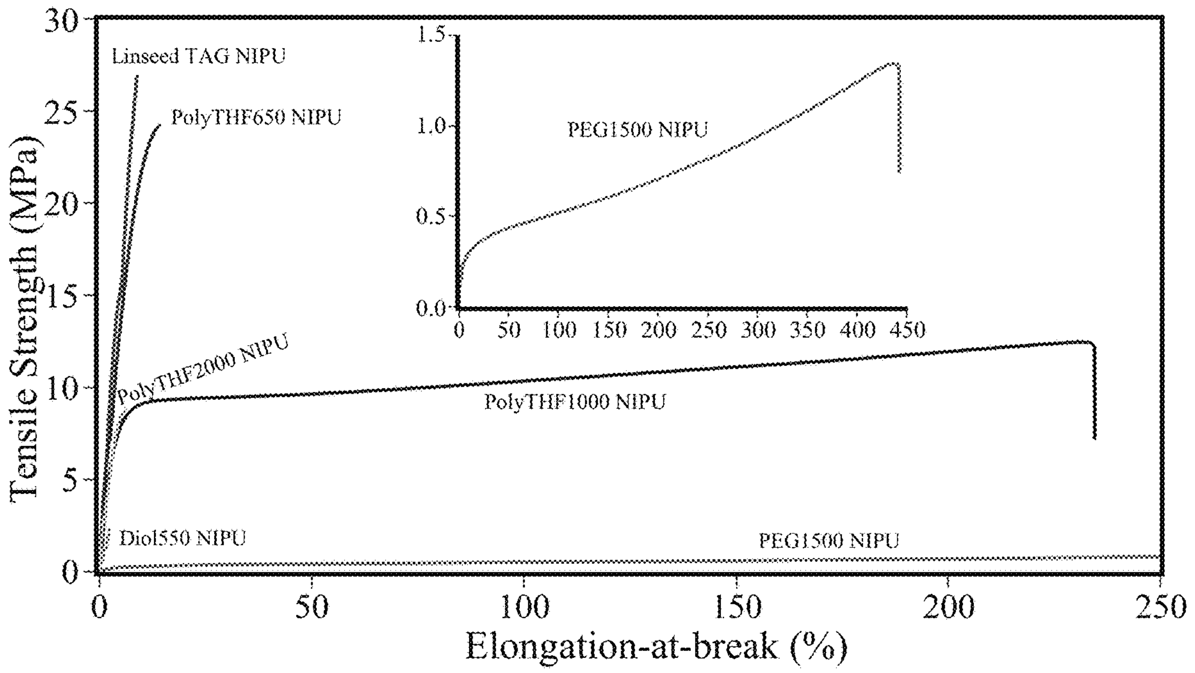
FIG. 15 illustrates tensile curves of NIPUs from PACM reaction with linseed TAG, linseed CC3 FAME, and CC3 diesters, according to some embodiments of the present disclosure.

The PEG1500 NIPU also showed elastomeric properties with 447% of elongation-at-break. However, the modulus, strength, and toughness are lower than those of the polyTHF1000 NIPU, due to the longer PEG chain. The tensile curves of the polyTHF1000 and PEG1500 NIPUs are shown in FIG. 15. The Diol550 NIPU was rigid due to the side chain nature of dimer acid diol. The excellent elastomeric performance of polyTHF1000 NIPU demonstrated the tensile properties can be tuned to desired level by using appropriate polyols.

Figure 16:
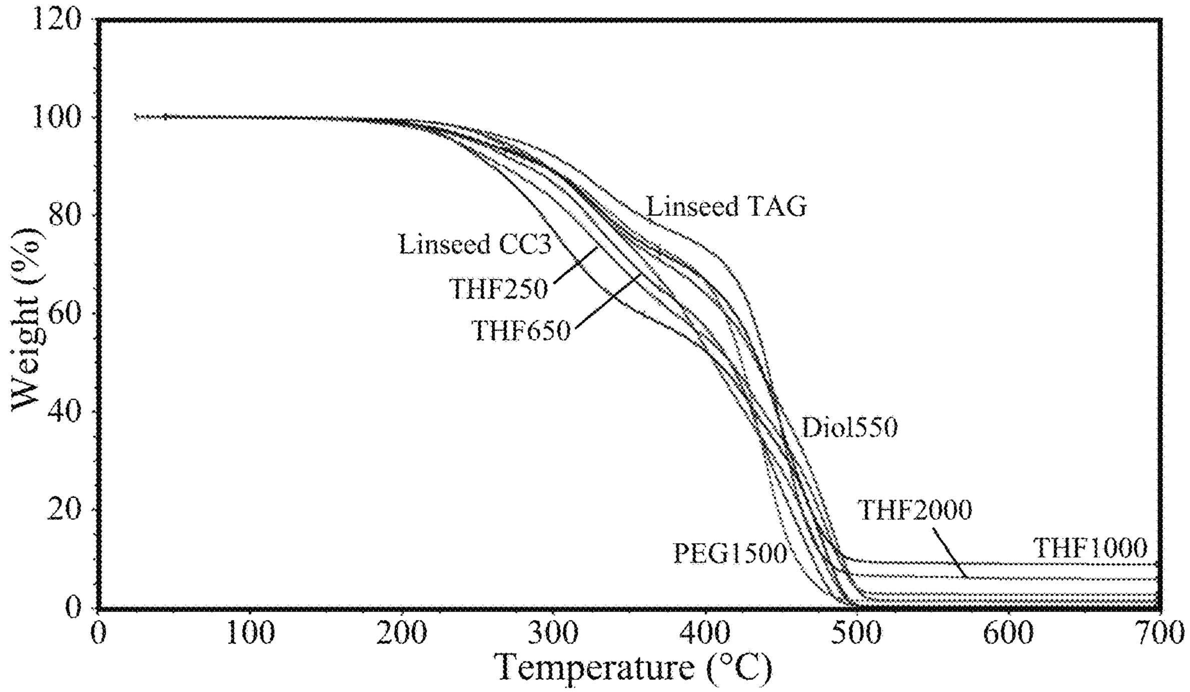
FIG. 16 illustrates TGA traces of NIPU from PACM reaction with linseed TAG, linseed CC3, and diesters cyclic carbonate, according to some embodiments of the present disclosure.

Thermal stability: TGA was applied to evaluate the thermal stability of the NIPUs generated for this report, and results are shown in FIG. 16, and the temperatures at which 10% of weight loss ($T_{d10}$%) occurring are listed in Table 4 above. Most of the NIPUs exhibited high thermal stability with $T_{d10}$% values of approximately 300° C. The linseed CC3 and polyTHF250 NIPUs had the lowest $T_{d10}$% values (259° C. and 266° C., respectively). Increasing the polyether chain length in the sequence from polyTHF250 to polyTHF2000 caused an increase in the $T_{d10}$%. In NIPU materials, the initial thermal degradation stage mainly related to decomposition of the hydroxy urethane linkages and minor degradation of the ether structure and fatty acid chain. These results show that the NIPUs with longer polyether chain have a lower content of hydroxy urethane group leading to a better thermal stability.

Experimental Methods

Materials: Epoxide linseed oil (EPOXOL 9-5) was supplied by ACS Technical Products. Polytetrahydrofuran (PolyTHF) 250, 650, and 1000 were obtained from Huntsman. PolyTHF 2000 was supplied by BASF. Polyethylene glycol 1500 (PEG1500), 4,4-diaminodicyclohexylmethane (PACM), and tetrabutylammonium bromide (TBAB) were purchased from Sigma-Aldrich. Dimer acid diol (Pripol 1040) was provided by Croda. Lipase from *Candida antarctica* B (Lipozyme CALB) was purchased from Novozymes.

Synthesis of epoxidized linseed oil fatty acid methyl ester (ELO FAME): ELO FAME was synthesized through a NaOH catalyzed transesterification reaction using a slightly modified method from previous literature, as shown in Scheme 3. First, epoxidized linseed oil (100.0 g), NaOH methanol solution (1.0 g NaOH in 30.0 g methanol), and acetone (5.0 g) were added to the reaction flask. This reaction was then carried out at room temperature for 1 h with magnetic stirring. After reaction, the liquid mixture was dissolved in ethyl acetate and washed by distilled water for three times to remove the residual NaOH catalyst and glycerol (byproduct). The remaining water in ethyl acetate was absorbed by $Na_2SO_4$, and the ethyl acetate was then removed by rotovap.

Synthesis of linseed oil fatty acid methyl ester cyclic carbonate (linseed CC FAME): Linseed CC FAME was synthesized through the carbonation reaction of ELO FAME, as shown in Scheme 3. The ELO FAME (100.0 g) and TBAB (5.0 g) were placed and reacted in a parr reactor at 140° C. with the $CO_2$ pressure of 500 psi for 12 h. The carbonation reaction progress was monitored via $^1$H NMR spectroscopy by the disappearance of the proton signals associated with the epoxide group. Upon completion, TBAB was removed by dissolving the mixture in ethyl acetate and washing three times with distilled water. The remaining water in ethyl acetate was absorbed by $Na_2SO_4$, and the ethyl acetate was then removed by rotovap. The dried linseed CC FAME were collected and stored for use.

Preparation of linseed oil fatty acid methyl ester enriched cyclic carbonate (linseed CC3 FAME): Linseed CC FAME was used to prepare the linseed CC3 FAME. Hexane and toluene (1:4, volume ratio) were added into linseed FAME carbonate (solvent:linseed CC FAME=5:1, weight ratio). The bottom layer was collected and the solvent in it was removed by rotovap. The solvent-free liquid from the bottom layer was then dissolved in the hexane/toluene mixture at same weight/volume ratio. The linseed CC3 FAME was obtained by repeating this procedure for three times. The purity of linseed CC3 FAME in the enriched fraction was about 85% which was calculated by $^1$H NMR. Ideally, the functionality of linseed CC3 FAME is 3, which means there are 3 cyclic carbonate groups in one linseed CC3 FAME molecule. Finally, the functionality of prepared linseed CC3 FAME sample was 2.85 indicating the 85% of purity. The yield was 35%.

Synthesis of CC3-derived diesters: CC3 diesters were synthesized through transesterification of linseed CC3 FAME and diols. Six types of CC3-derived diesters were synthesized from various diols including PolyTHF250, 650, 1000, 2000, PEG1500, and fatty acid dimer diol (Diol550), as shown in Table 2 and Reaction 1 above. Typically, linseed CC3 FAME (0.04 mol), diol (0.016 mol), toluene, (0.4 mol), and lipase from *Candida antarctica* B (10 wt. % of reactants) were added to the reaction flask on a magnetic stirrer. Then the mixture was stirred at 60° C. for 5 days. The methanol byproduct was removed by vacuum every 24 h to push forward the reaction. The reaction progress was monitored via $^1$H NMR spectroscopy by the appearance of the proton signals associated with the synthesized ester group. After the reaction completion, the product was washed with methanol to remove unreacted linseed CC3 FAME. The remaining layer was then rotary evaporated to remove all remaining toluene. The CC3-derived diesters was named by the diols used for its synthesis.

NIPU synthesis: A series of NIPUs were synthesized by the aminolysis reaction between CC3-derived diesters and PACM. Stoichiometric amounts of CC3-derived diesters and PACM were placed into a speedmixer jar, then the mixture was mixed by SpeedMixer at 3000 rpm under vacuum for 2 minutes. After that, the solvent-free mixture was stirred at 70° C. for 1-30 minutes before it was poured into polytetrafluoroethylene mold. Thereafter, the product was cured at 70° C. for 12 hours and 110° C. for 12 hours in a vacuum oven. Table 4 above summarizes compositions of NIPU.

Analytical methods: All samples were characterized by a Nicolet iS50 Fourier transform infrared (FTIR) spectroscopy with attenuated total reflectance (ATR) from 4000 to 400 $cm^{-1}$ at room temperature. Sixteen scans of each sample were taken with a resolution of 4 $cm^{-1}$. NMR tests were conducted using the Bruker 300 and 400 MHz NMR spectrometer. Viscosity measurements were done by a Rheometer (TA Instruments) from 25 to 100° C. at 10 rad/s with 1.0% strain. Differential scanning calorimetry (DSC, TA Instruments) was employed to determine the glass transition temperature (Tg) of NIPU. The experimental temperature was increased from −85 to 150° C. with a rate of 10° C./min under nitrogen purge. In addition, the thermal history of the sample was erased before the DSC data recording. Thermogravimetric analysis (TGA, TA Instruments) was employed to characterize the thermal stability of NIPU. The samples (around 10 mg) were heated with a rate of 10° C./min from room temperature to 700° C. Then, $T_{d10\%}$ was recorded as the temperature at which 10% of weight loss take place.

Instron tester was used to measure the tensile properties of NIPU including Young's modulus, tensile strength, elongation-at-break, and toughness. Toughness was determined by integrating the stress-strain curve. The samples were cut with a length of 60±1 mm, a width of 12.5±1 mm, a thickness of 2±0.5 mm. The tests were carried out at room temperature with a fixture moving speed of 10 mm/min. Tensile properties are reported as the average of at least three tests.

The embodiments described herein should not necessarily be construed as limited to addressing any of the particular problems or deficiencies discussed herein. References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target. The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A composition comprising

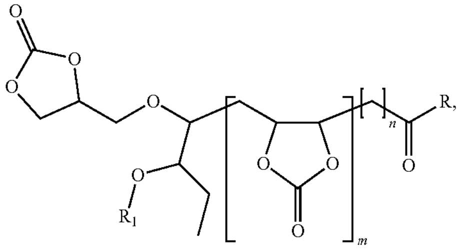

wherein:

n is between 0 and 20, inclusively, m is between 0 and 20, inclusively,

R comprises at least one of carbon, hydrogen, or oxygen, and $R_1$ comprises at least one of carbon, hydrogen, or oxygen.

2. The composition of claim 1, comprising

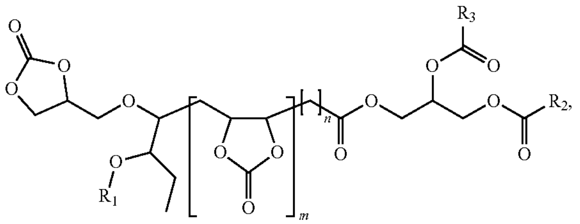

wherein:

$R_2$ comprises at least one of carbon, hydrogen, or oxygen, and $R_3$ comprises at least one of carbon, hydrogen, or oxygen.

3. A composition comprising:

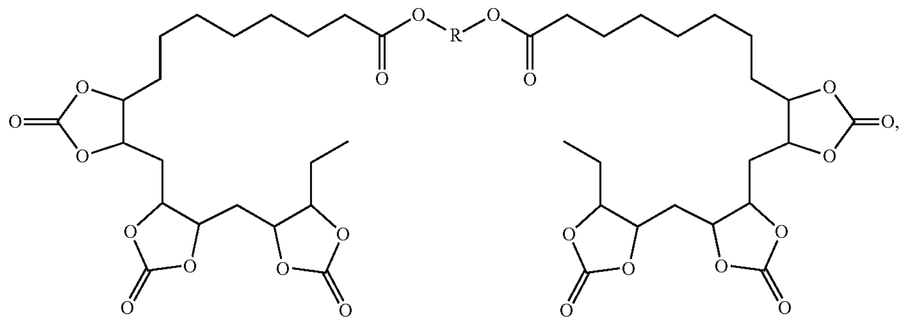

wherein:

R comprises

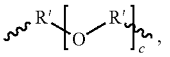

c is between 0 and 500, inclusively, and

R' is a straight hydrocarbon chain having between 1 and 18 carbon atoms, inclusively.

4. A composition comprising

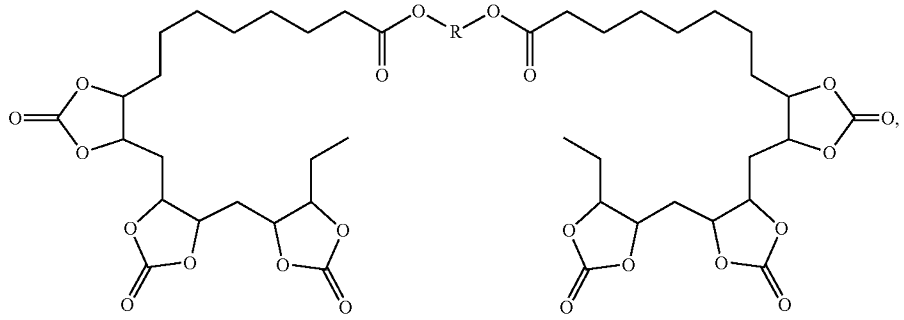

wherein R comprises

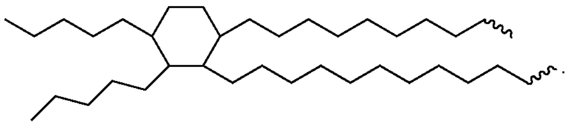

5. A composition comprising:

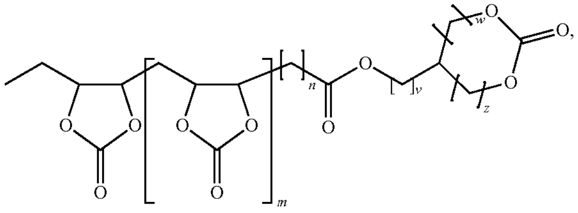

wherein:

n is between 0 and 20, inclusively, m is between 0 and 20, inclusively, v is between 0 and 10, inclusively, w is between 0 and 3, inclusively, and z is between 0 and 3, inclusively.

6. The composition of claim 5 comprising at least one of

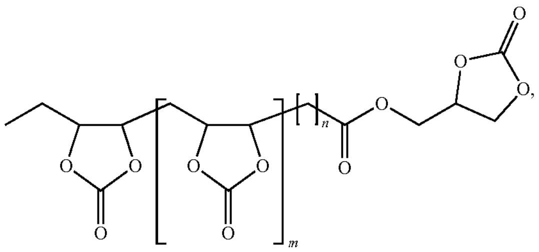

or

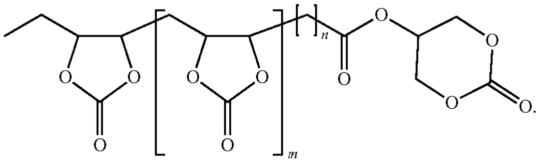

7. A composition comprising
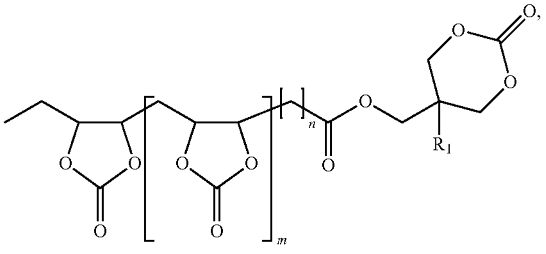
wherein
n is between 0 and 20, inclusively,
m is between 0 and 20, inclusively, and
$R_1$ comprises carbon and hydrogen.
8. The composition of claim 7, comprising
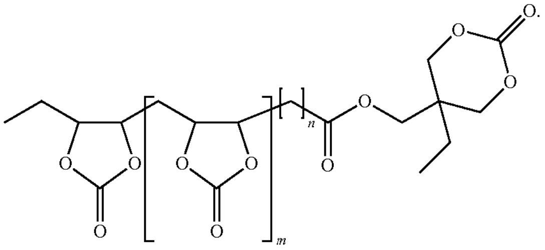
9. A composition comprising at least one of
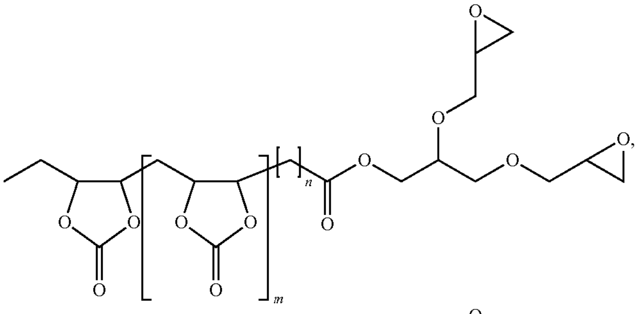
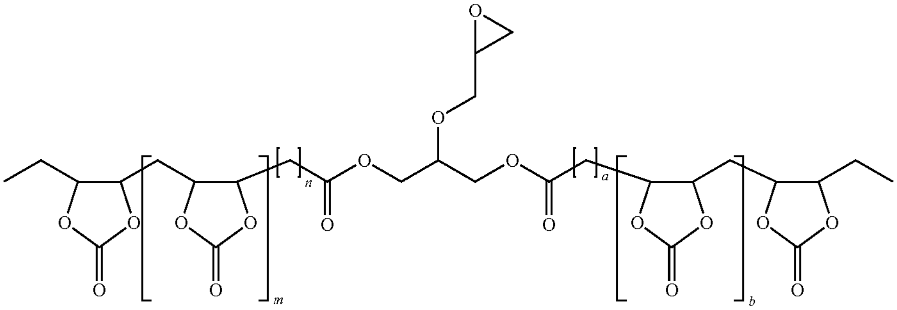
, or
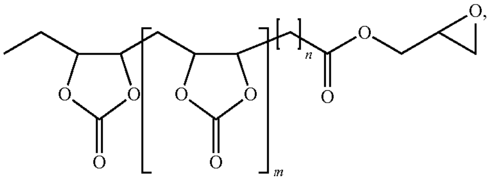
wherein:
n is between 0 and 20, inclusively,
m is between 0 and 20, inclusively,
a is between 0 and 20, inclusively, and
b is between 0 and 20, inclusively.
* * * * *